United States Patent [19]
Muderlak et al.

[11] Patent Number: 5,175,791
[45] Date of Patent: Dec. 29, 1992

[54] FRAGRANCE DIFFUSER HAVING STEPPED POWER LEVELS

[75] Inventors: Kenneth J. Muderlak, Shorewood; Patrick Maloney, Madison, both of Wis.; Tsung-Ying Hsieh, Hsin Chu, Taiwan

[73] Assignee: Technical Concepts, L.P., Chicago, Ill.

[21] Appl. No.: 598,421

[22] Filed: Oct. 16, 1990

Related U.S. Application Data

[63] Continuation-in-part of Ser. No. 521,981, May 7, 1990.

[51] Int. Cl.⁵ ............................................. A05B 1/02
[52] U.S. Cl. ..................................... 392/390; 219/497; 219/492; 219/501; 422/122
[58] Field of Search ............... 219/497, 492, 493, 501, 219/506; 422/122; 392/390

[56] References Cited

U.S. PATENT DOCUMENTS 4,705,930  11/1987  Sathre, Jr. et al. ............... 219/492
5,012,961   5/1991  Madsen et al. ..................... 222/643

*Primary Examiner*—Mark H. Paschall
*Attorney, Agent, or Firm*—Welsh & Katz, Ltd.

[57] ABSTRACT

A fragrance diffuser (100) comprises a housing defining a chamber (116) for holding a fragrance-emitting block (110), a heating element (112) located within the housing, a timing and indicating circuit board (114) to signal when the predicted life of the fragrance emitting block has expired, a power supply connection plug (134) for providing electrical power to the heating element and the timing and indicating board, and a keying system (234, 236, 238) incorporated in the chamber (116) and on the fragrance-emitting blocks (110). The blocks are encoded or keyed to indicate that they possess particular predefined characteristics, such that only blocks having those characteristics may be inserted. The diffuser is constructed with a downwardly-projecting housing extension (132) for the power supply connection to allow the use of an adjacent electric power outlet when the diffuser is properly installed. The diffuser also includes an indicator LED (156) to indicate when a timing interval, corresponding to the life of a fragrance block inserted therein, has expired, wherein the timing interval is reset by a switch (182) only at the request of a user. Various circuit embodiments are disclosed for increasing the power applied to the heating element over time, since the aroma strength of a fragrance block decreases over time.

43 Claims, 10 Drawing Sheets

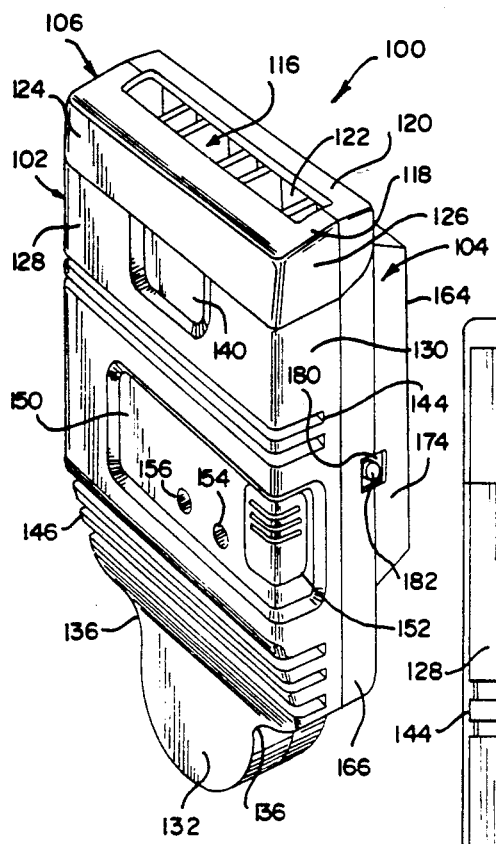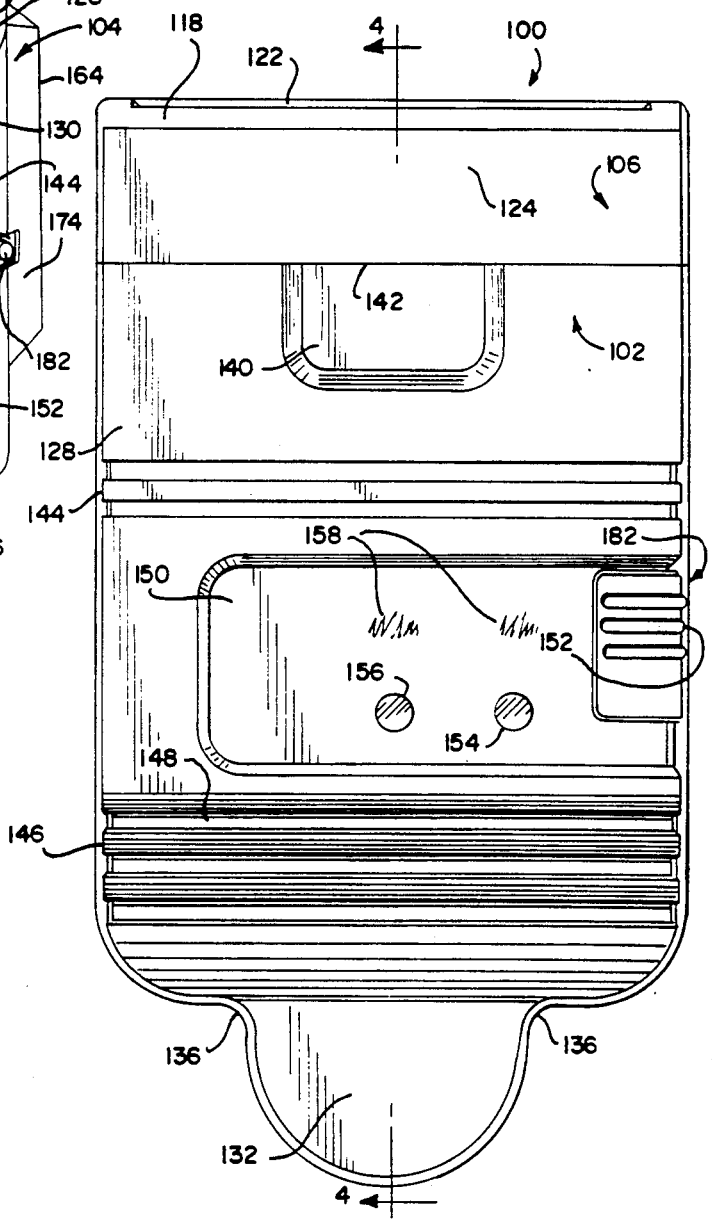

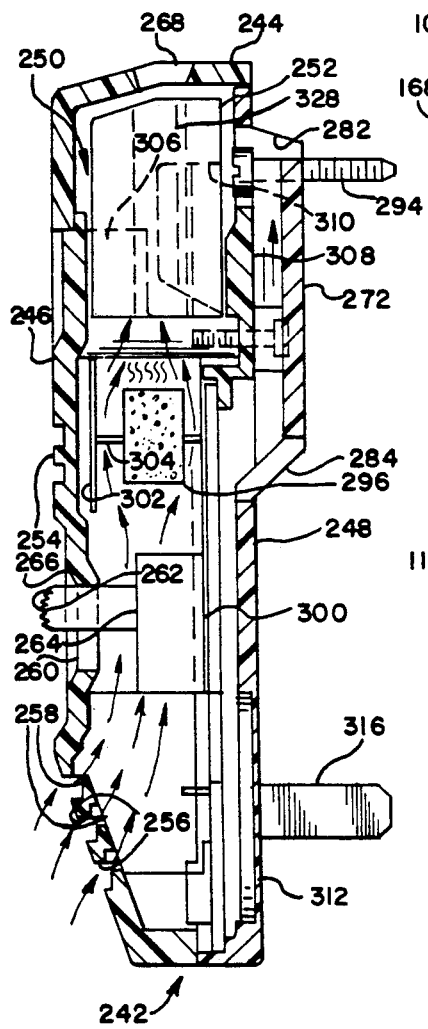
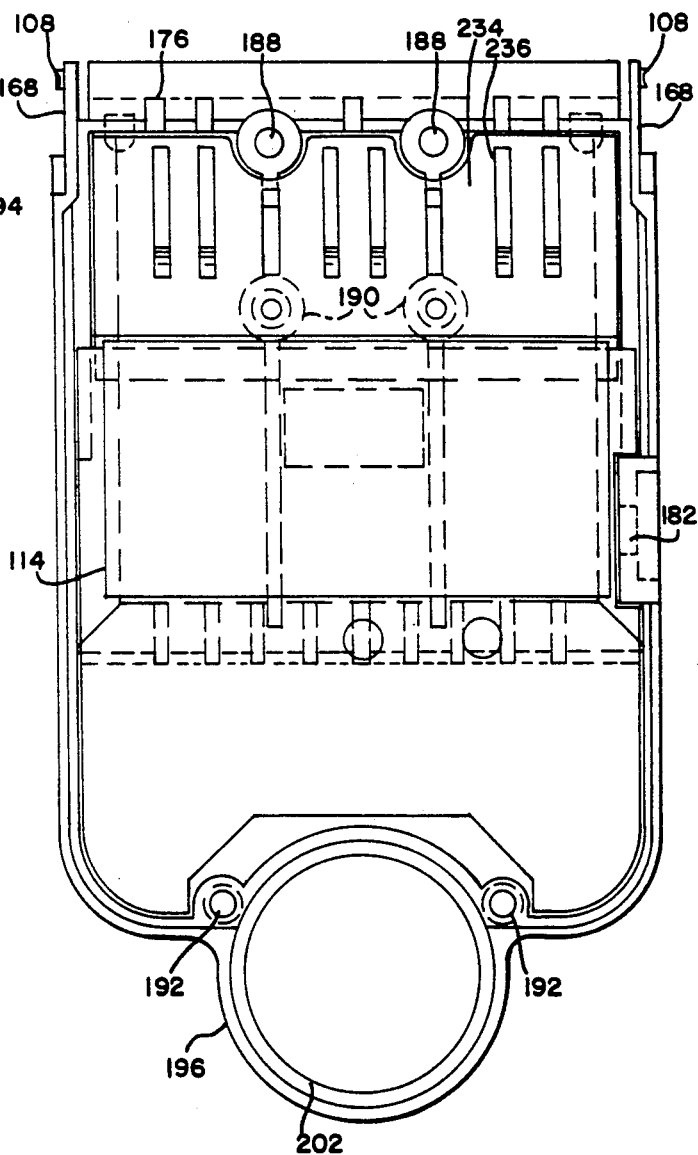

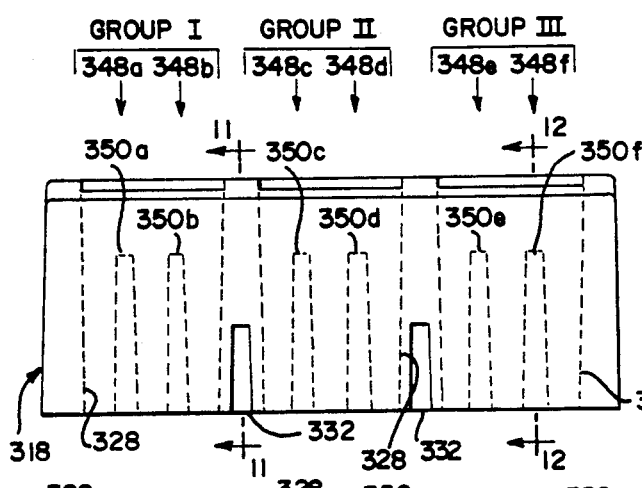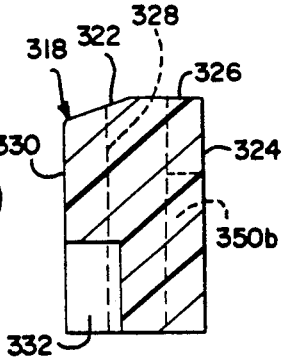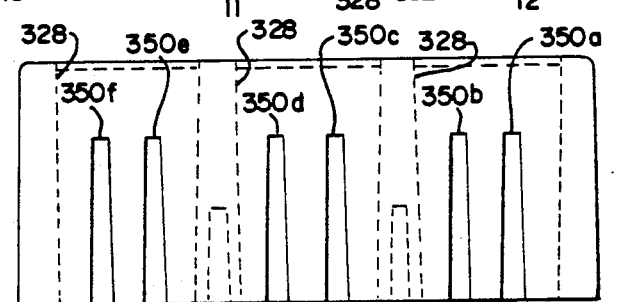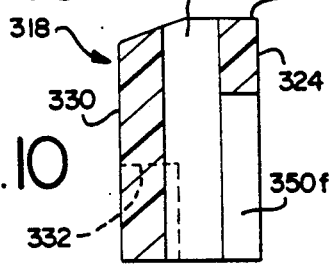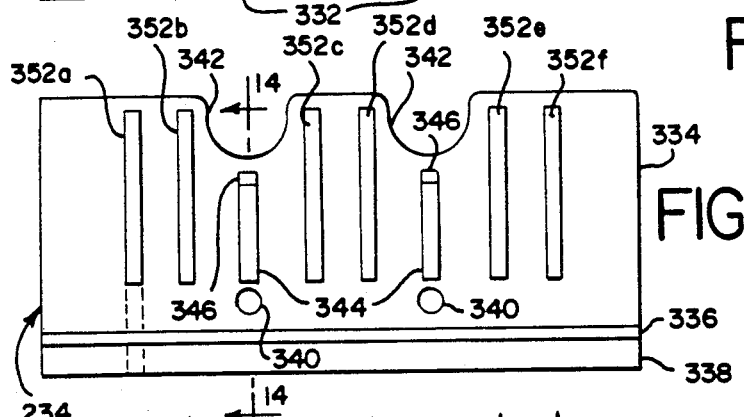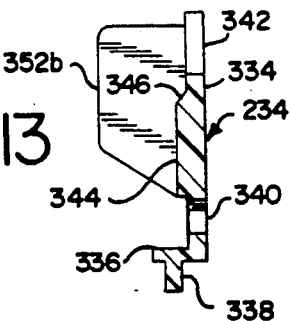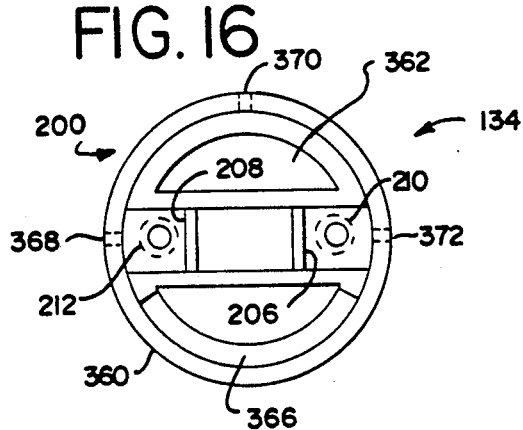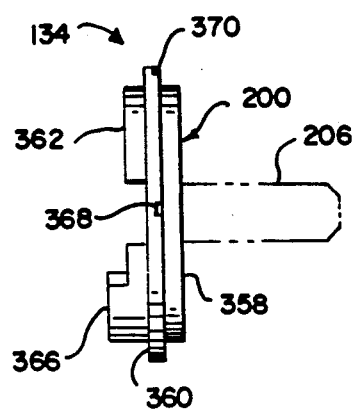

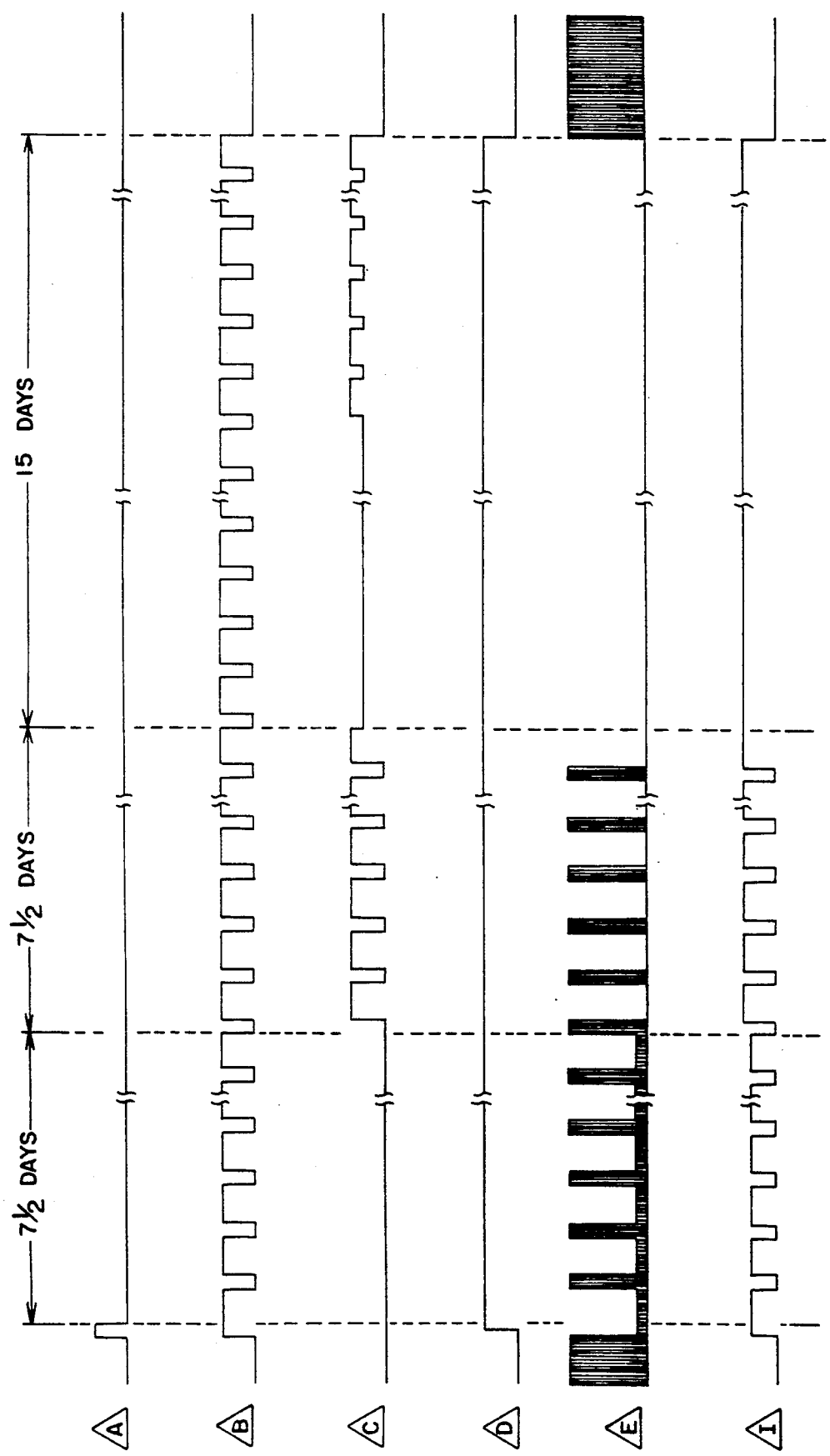

FRAGRANCE DIFFUSER HAVING STEPPED POWER LEVELS

CROSS-REFERENCE TO RELATED APPLICATIONS

This application is a continuation-in-part of application Ser. No. 07/521,981, filed May 7, 1990 now pending, entitled "Fragrance Diffuser", which is assigned to the same assignee as the present application.

BACKGROUND OF THE INVENTION

This invention generally relates to fragrance dispensing devices and, more particularly, to devices which dispense fragrance from an aroma bearing media by passing a current of warm air near or though the media to enhance diffusion of the fragrance into the adjacent air.

Operators of commercial buildings with interior spaces exposed to the public, and in particular hotel and motel operators, often desire to provide a consistent, pleasant fragrance in those spaces. A variety of devices and methods have been developed for dispensing, on a controlled basis, an appropriate fragrance into a room environment. For example, a number of devices have been developed which periodically dispense a gas or volatile liquid fragrance media from a closed container directly into the air. The fragrance media may be stored at elevated pressure and merely released, or may be actively pumped from the container. While these devices may be acceptable for some purposes, they are inappropriate for hotel guest rooms in that their periodic dispensing produces undesirable noise and sharp variations in the perceived strength of the fragrance. To be effective, these devices must be in an area of free air circulation, and thus are typically mounted in a prominent location on an exposed wall, which may be aesthetically objectionable.

To avoid these and other disadvantages, various fragrance dispensing devices have been developed which provide a continuously exposed fragrance bearing surface and which rely on natural diffusion of the fragrance media into the air, either unaided, or enhanced by temperature, air flow rate, or the like. At least one of these dispensers has a porous pad of cloth or the like which is impregnated with the fragrance bearing media. U.S. Pat. No. 4,804,821 discloses a diffusion dispenser using a fragrance-emitting block impregnated with an aroma bearing media. The block is located in a user-accessible chamber so that it may be conveniently replaced when the media is expended. A heater located below the block provides a current of warm air to enhance diffusion. The block has a number of chimney-like vents running vertically therethrough to permit the air current to flow through the block, thereby increasing the effective fragrance-diffusing surface area exposed to the air. The heater is thermostatically controlled using a sensor located above the heater when the diffuser is in its normal upright orientation. The diffuser has a rotating electrical supply plug to permit the diffuser to be installed in an upright orientation regardless of the orientation of an available wall outlet.

The diffusers of the prior art exhibit a number of significant disadvantages. One problem is safety. The thermostats of the prior art diffusers are located above the heater when the diffuser is installed in its normal orientation. Because convection air currents normally flow upward, if a diffuser is incorrectly installed, for example, in a non-upright orientation, the thermostat will be located below or to the side of the heater and will not be actuated by the rising current of warm air. Thus, the thermostat will permit the heater to operate continuously, possibly causing a fire or damage to the diffuser.

Another safety problem is the ease with which "foreign" fragrance blocks (i.e., a fragrance block not specifically designed to work in the particular diffuser, which may lack design features required for safe operation) and other foreign objects may be inserted into the heated fragrance block chamber. In prior art diffusers, any object which does not exceed the boundaries of the diffuser's heated fragrance block chamber may be inserted therein. An uninformed user who runs out of the intended fragrance blocks, for example, may be tempted to insert a fragrance block designed for a non-heated dispenser, or even a bar of soap. These objects may lack the necessary vent channels to prevent overheating of the heater element.

An analogous operational problem is presented by the desire of institutional users to provide a certain selected aroma in a particular area, and a different selected aroma in another area. It is difficult to ensure compliance with such desires by maintenance, housekeeping, or other personnel who may replace expended fragrance blocks, because prior art diffusers will accept any block which does not exceed the boundaries of the diffusion chamber.

Another operational problem with prior art diffusers is that their relatively high-temperature, thermostatically-controlled heaters operate intermittently, thereby causing noticeably sharp variations in the perceived fragrance intensity. Hotel and other public accommodations operators prefer that guests perceive a consistent level of pleasant fragrance, rather than occasional sharp fragrance bursts. A further operational disadvantage of the prior art diffusers is that their power supply plugs are so located that the diffuser housing obscures adjacent power receptacles, preventing use of those receptacles.

Prior art diffusers present a further operational problem in that they do not effectively indicate when the aroma-bearing media in the fragrance block is expended. U.S. Pat. No. 4,795,883 discloses a fragrance diffuser having a timer circuit which measures a predetermined period of elapsed time corresponding to the predicted life of the diffuser block, and when exceeded, presents a visual indicator or disables the heater. The timer is reset by a sensing switch actuated when a fragrance block is inserted or removed. This causes inaccurate results as the user may wish to remove the fragrance block before it is expended, for example, to inspect the block to determine which fragrance it contains, without starting a new timing period.

Disabling the heater after the timer has expired is undesirable because even after the predetermined period, the fragrance block will typically still contain a sufficient amount of aroma media to provide effective (if not optimal) air treatment. Disabling the heater thus prevents the diffuser from operating at all during the period between the timer expiration and the time the user notices the indicator, so that the room is entirely deprived of fragrance treatment during this period.

A further problem with prior art diffusers is related to the characteristics of the aroma-bearing cartridge. Due to the present chemistry of the cartridge, the apparent level of fragrance released from the cartridge is not constant over the life of the cartridge. An excessive fragrance level is particularly noticeable during the first few days after the installation of a new fragrance cartridge. Therefore, if a constant level of heat is applied to the cartridge over its life cycle, then the fragrance seems to be too strong at the beginning of the life cycle, and too weak at the end of its life cycle. This apparent changing of the fragrance levels, which is typical of most solid cartridge fragrance blocks, is highly undesirable.

Thus, a need exists for a method and means for controlling the fragrance level of a solid cartridge block over its life cycle.

OBJECTS AND SUMMARY OF THE INVENTION

It is therefore an object of the present invention to provide a fragrance diffuser which permits the insertion of only appropriately designed fragrance emitting blocks into the heated chamber of the diffuser.

It is another object of the invention to provide a fragrance diffuser which permits the insertion of only fragrance emitting blocks which possess particular predefined characteristics into the heated diffusing chamber of the diffuser.

It is a further object of the invention to provide a fragrance diffuser which provides a substantially consistent level of fragrance diffusion.

It is still another object of the invention to provide a fragrance diffuser which allows the use of adjacent electric power outlets when the diffuser is properly installed.

It is yet another object of the invention to provide a fragrance diffuser having a circuit to indicate when a timing interval, corresponding to the life of a fragrance block inserted therein, has expired, wherein the timing interval is restarted only at the request of a user.

It is still a further object of the invention to provide a method and means for stabilizing the fragrance level over the life cycle of the fragrance block.

A first embodiment of a fragrance diffuser according to the present invention comprises a housing defining a chamber for holding a fragrance emitting block, a heating device located within the housing, a timing and indicating device to signal when the predicted life of the fragrance emitting block has expired, a power supply connection plug for providing electrical power to the heating device and the timing and indicating device, and a key system incorporated in the chamber and on the fragrance emitting block to permit insertion of only predefined fragrance blocks in the chamber. The preferred heater operates continuously at a relatively low temperature to provide a consistent level of emitted fragrance, to eliminate the need for a thermostat, and to obviate potential safety problems in case the diffuser is installed in an incorrect orientation or in case inadequate ventilation is provided. The power supply connection plug is located in a narrow downward-extending portion of the diffuser housing so that another power outlet, which may be adjacent to the one required for the diffuser, is not blocked by the housing. A preferred timer and indicator circuit includes a user-operated reset switch which restarts the timing period and appropriate circuitry to prevent unintended reset operations.

The preferred chamber/block key system embodiment comprises a total of six predefined positions (three groups of two positions each) within the heated diffuser chamber, including key tabs which extend perpendicularly from a key plate located on the chamber wall. Six matching positions are predefined for key tab slots in corresponding fragrance emitting blocks to be inserted into the diffuser. Under the preferred key scheme, for each of three key tab position groups, one of the available positions is always occupied, and the remaining position is always unoccupied, resulting in a total of eight unique key position combinations. The inwardly-protruding key tabs prohibit insertion into the chamber of any fragrance-emitting block which does not contain at least a matching slot for each tab. Particular key combinations may be associated with certain diffuser characteristics or user-selected fragrances. The key system also ensures that all fragrance blocks and diffusers are manufactured in conformance with the preferred key scheme, as the key system will permit insertion of only correct blocks in each diffuser.

The present invention also provides an improved method and means for controlling the fragrance level emitted from the fragrance block within the first few days of operation. Electronic circuitry is included within the fragrance diffuser which varies the amount of power to the heating elements over time, thus increasing or decreasing the temperature applied to the fragrance block. In a preferred embodiment, a resistor is inserted in series with the heating element such that it reduces at least a portion of the power applied to the heating element for a given period of time. A timer circuit measures the time of operation and produces a number of timing signals after each given period of time has expired. A switch mechanism, such as a silicon controlled rectifier (SCR), is connected to the resistor such that it controls the amount of power delivered to the heating element over time.

Various embodiments are presented in which the circuit can increase the amount of power applied to the heating element in at least four ways, or in any combination thereof: (a) removing a series resistor from the circuit such that the voltage applied to the heating element is increased after a period of time; (b) switching in a second or substitute heating element such that additional heat is applied after a period of time; (c) increasing the duty cycle of the signal applied to the heating element switching mechanism, such that the "on" periods for the heating element become greater and/or the "off" periods become less over time; and (d) increasing the conduction angle for the SCR operating from an alternating current, such that current flows through the heating element during greater portions of the AC voltage cycle over time.

In the preferred embodiment, the heating element produces an average of 3.0 watts for the first 7½ days of operation, i.e., operating at 4.0 watts at a 75% duty cycle (31.5 minutes on and 10.5 minutes off) and operating in series with a resistor. From 7½ days to 15 days, the resistor is switched out of the circuit such that the same 75% duty cycle is applied to the 4.8 watt heating element directly without the resistor in series, thus averaging 3.6 watts. From 15 days to 30 days, the 75% duty cycle is eliminated such that 4.8 watts is dissipated continuously by the heating element. After 30 days has expired, which approximates the life cycle of the fragrance block, the circuit enables a red indicator light, and turns off the heating element. If a reset button is momentarily pressed, power is again applied to the heating element (4.0 watts) while the indicator light stays on, without resetting the timing cycle. If the reset switch is held for greater than two seconds, the timing cycle is restarted, and the indicator light is turned off.

BRIEF DESCRIPTION OF THE DRAWINGS

The preferred embodiments of a diffuser according to the present invention will be best understood with reference to the attached drawings, in which:

FIG. 1 is a perspective view of a first embodiment of a fragrance diffuser according to the present invention;

FIG. 2 is a front elevation view of the diffuser of FIG. 1;

FIG. 5 is a front elevation view of the diffuser of FIGS. 1-4 in which the housing cover has been removed;

FIG. 7 is a cross-sectional view of the diffuser of FIG. 6 taken along line 7—7;

FIG. 9 is a front plan view of the fragrance block of FIG. 8;

FIG. 10 is a rear plan view of the fragrance block of FIG. 8;

FIG. 11 is a cross-sectional view of the fragrance block of FIG. B taken along line 11—11 of FIG. 9 and showing the details of an alignment slot;

FIG. 12 is a cross-sectional view of the fragrance block of FIG. 8 taken along line 12—12 of FIG. 9 showing the details of a key slot;

FIG. 13 is a front elevation view of the key plate of the diffuser of FIG. 8;

FIG. 14 is a cross-sectional view of the key plate of FIG. 13 taken along line 14—14 of FIG. 13 showing the details of a key tab;

FIG. 16 is a front plan of a rotating power supply plug according to the present invention;

FIG. 17 is a side elevation view of the rotating power supply plug of FIG. 16;

FIG. 24 illustrates representative voltage waveforms for various points in the circuit shown in FIG. 23.

DETAILED DESCRIPTION OF THE PREFERRED EMBODIMENTS

Figure 3:
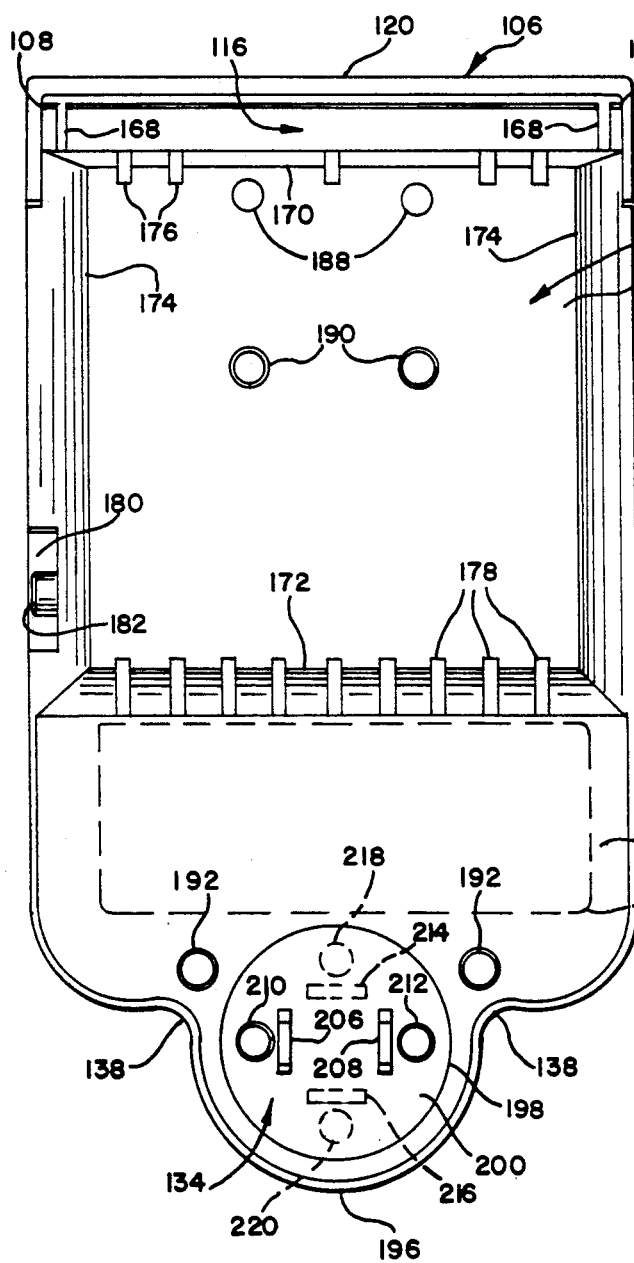
FIG. 3 is a rear elevation view of the diffuser of FIG. 1.
Figure 4:
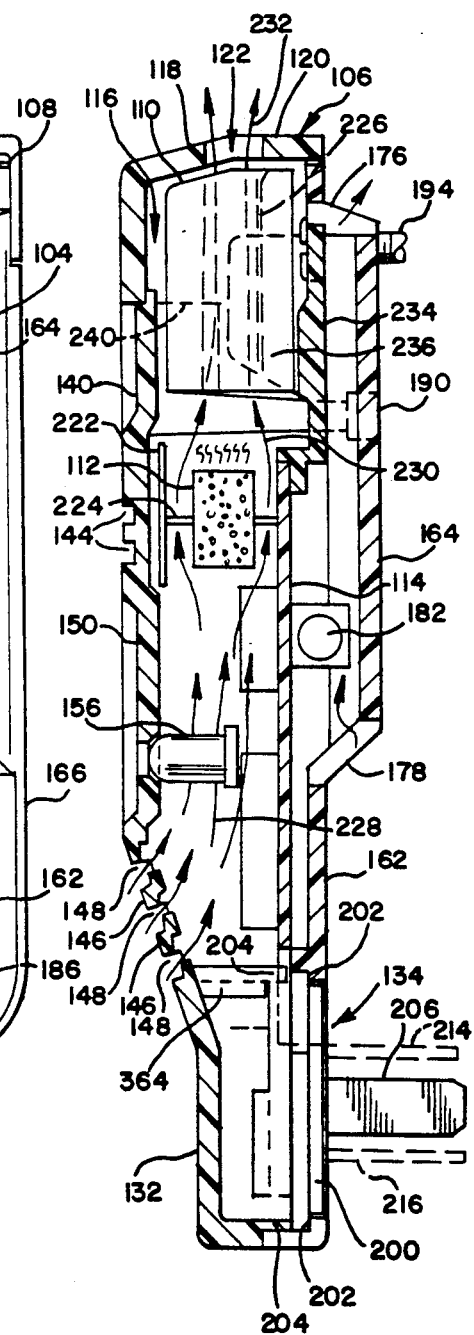
FIG. 4 is a cross-sectional view of the diffuser of FIG. 1 taken along the line 4—4 of FIG. 2.

Referring generally to the Figures and particularly to FIGS. 1-4, there are shown perspective, front, rear, and cross-sectional views, respectively, of a first preferred embodiment of a fragrance diffuser generally constructed in the shape of parallelepiped and according to the present invention. Diffuser 100 has a housing comprising a front cover 102, a rear cover 104, and a lid 106. In normal use, front cover 102 is attached to rear cover 104 using suitable fastening means (not shown). Lid 106 is pivotally attached to rear cover 104 by suitable pivot 108 (FIG. 3). These three housing elements define an interior space to contain working parts of the diffuser 100, including a removable fragrance-emitting block or cartridge 110 (FIG. 4), heating element 112 (FIG. 4), and timing and indicating board 114 (FIG. 4). The fragrance-emitting block 110 resides in an upper region or chamber 116 of the interior space; lid 106 pivots upward to allow convenient user access to chamber 116 for ease of insertion and removal of the fragrance-emitting block 110. Lid 106 is shown in its closed position in FIGS. 1-4.

Referring to FIG. 4, lid 106 has a top surface preferably comprising adjacent front and rear planar sections 118, 120 respectively. An elongated vent aperture 122 in surfaces 118, 120 leads into the fragrance block chamber 116 to permit fragrance-laden air to escape to the atmosphere when the diffuser 100 is in operation. Rear section 120 of the top surface is preferably substantially perpendicular to the vertical axis of the diffuser 100. Front section 118 is preferably angled slightly downward toward the front of the diffuser 100. Front wall 124 and side walls 126 extend downward from top sections 118, 120, forming a substantially rectangular partial box, and in the closed lid position, these walls 124, 126 sit flush with mating front cover walls 128, 130. In order to permit pivoting about pivot 108, lid 106 has no rear wall.

Front cover 102 includes a front wall surface 128, and a pair of side wall surfaces 130 extending rearward toward the rear cover 104. The upper portion of the front wall 128 is substantially planar, excluding surface detail. The lower portion of the front wall 128 is angled rearward, culminating in a narrowed semicircular projection 132 of the diffuser 100 which houses a rotating power supply plug 134. The front and rear covers 102, 104 are narrowed in areas 136, 138, respectively, to create this projection, and therefore include corresponding semicircular projection 132. Housing the plug 134 in such a projection prevents obscuring the electrical wall outlet adjacent the one used for the diffuser 100.

Front cover 102 preferably includes a number of surface details to improve both performance and appearance. A first shallow depression 140 in front wall surface 128 exposes an engaging surface 142 on the front wall 124 of lid 106, permitting easier lifting of lid 106 with a user's finger. Upper and lower sets of decorative striations 144, 146 wrap horizontally across the exterior of the front cover 102 including front wall 128 and side walls 130. A plurality of front ventilation intake openings 148, which may be slots or holes, are provided and are preferably visually obscured by the lower striations 146.

A second shallow depressed area 150 in front wall surface 128 provides a location for on-off switch actuator 152, on-off indicator 154, elapsed time indicator 156, and labelling 158. Switch actuator 152 is operatively connected to the operating arm of an on-off switch 160 (FIG. 19) disposed underneath the actuator 152, and is preferably slidably mounted for short upward or downward translations as necessary to operate the switch to its on and off positions. Switch 160 (FIG. 19) controls operating power to the heating element 112 (FIG. 4). On-off indicator 154 illuminates when operating power is available to the heating element 112. Elapsed time indicator 156 illuminates to warn the user that a predetermined period of operation has elapsed (e.g. 30 days) and that the fragrance-emitting block 110 is therefore exhausted. Each of these elements 152, 154, 156 must protrude slightly from an exterior surface for proper operation. Locating them in depressed area 150 permits them to protrude slightly from that area without extending beyond the front wall surface 128, thereby minimizing potential damage from objects which may come into contact with the housing. Labelling 158 preferably indicates the function of elements 152, 154, and 156 and may provide operating instructions to the user.

Referring to FIG. 3, rear cover 104 includes a lower rear surface 162, an upper raised rear surface 164, and exterior side walls 166. Support tabs 168 for pivot 108 (used to mount lid 106) extend upward from side walls 166. Upper, lower, and side raised surface support walls 170, 172, 174 respectively extend angularly rearward from side walls 166 to raised surface 164. A plurality of upper ventilation intake openings 176, and lower ventilation intake openings 178, which may be slots or holes, are provided in upper and lower raised surface support walls 170, 172 respectively to permit ambient room air to enter the diffuser 100. Raised surface 164 provides additional space within the upper chamber 116 of the diffuser 100, and provides a predetermined ventilation clearance between the lower portion of the diffuser 100 and the wall surface (not shown) to which it is attached during normal use. Moreover, since upper rear surface 164 is raised approximately 0.25 inches from lower rear surface 162 (which is the approximate distance that a wall plate for a standard 110 VAC power outlet projects from the wall), then diffuser 100 would be substantially flush with the wall when mounted.

Notch 180 (FIG. 3) in side wall 166 permits the operating arm of timer reset switch 182 to protrude from the side of the rear cover 104. The user may actuate this switch 182 (typically when replacing fragrance-emitting block 110) to reset the elapsed timer circuit 184 (FIG. 19), thereby extinguishing elapsed time indicator 156.

The lower rear surface 162 of rear cover 104 has a labelling area 186 for the display of instructions to the user, safety warnings, and other information.

Several sets of holes 188, 190, and 192 are provided in rear cover 104 to permit the rear cover 104 to be secured to front cover 102 using appropriate fasteners (not shown), and to permit the entire diffuser 100 to be secured to a vertical wall surface (not shown) if desired using suitable fasteners 194 (FIG. 4). Nevertheless, the entire diffuser 100 can be entirely self-supported against the wall using only the power supply plug 134.

The lower portion of the rear cover 104 has a narrowed semicircular projection 196 in which rotating power supply plug 134 is mounted. The lower rear surface 162 of rear cover 104 is narrowed in areas 138 to create this projection. Housing the plug 134 in such a projection prevents obscuring the electrical wall outlet adjacent the one into which the diffuser 100 is plugged.

The details of rotating plug 134 are visible in FIGS. 3 and 4. A circular opening 198 is provided in the lower rear surface 162 to accommodate a circular support disk 200. Disk 200, which is preferably fabricated from an electrically insulating plastic material, is mounted for rotation between guide 202 (FIG. 4) on rear cover 104 and guide 204 on front cover 128. First and second electrical plug contact members 206, 208, extend rearward from disk 200 for insertion into a conventional electrical wall outlet (not shown). Holes 210, 212 are provided for appropriate fastening means (not shown) used to secure electrical wires to contact members 206, 208, and to secure contact members 206, 208 to disk 200.

Because diffuser 100 relies on convection for proper operation, as will be discussed later in greater detail, diffuser 100 must be mounted in a vertical orientation, as shown in the drawings. Plug 134 rotates approximately 180 degrees to permit the diffuser 100 to occupy a vertical orientation regardless of the orientation of the receiving wall outlet. In FIGS. 3 and 4, plug 134, contact members 206, 208, and fastener holes 210, 212 are shown in solid lines in a first orientation. These same elements are shown in phantom in a second orientation rotated 90 degrees clockwise from the first as 214, 216, 218, and 220 respectively.

Various features of the internal construction of diffuser 100 are shown in FIGS. 4 and 5. The timing and indicating board 114 is located toward the middle rear section of the diffuser 100, and heating element 112 is attached to board 114. Heating element 112 may be any appropriate known design consuming approximately 3 to 5 watts and producing a convective heated air output temperature, measured at the base of the fragrance block, of approximately 130 to 150 degrees Fahrenheit, such as a conventional wire-wound ceramic-body resistor of suitable resistance and power-handling capability. Heater power consumption and temperature specifications may vary, depending upon the particular diffuser embodiment and/or the particular fragrance block used.

Heating element 112 is attached to timing and indicating board 114 using an appropriate fastening and standoff mechanism (not shown), a predetermined clearance being provided around heating element 112 for proper air circulation. Thermal insulator 222, which may be a flat mica sheet or other appropriate material is preferably disposed via appropriate standoffs 224 between heating element 112 and the front wall 128 of front cover 102 to prevent damage to the material from which the cover is constructed. A similar insulator (not shown) may be provided to protect timing and indicating board 114.

Fragrance-emitting block 110 is disposed in region 116 above heating element 112, and contains a plurality of vertical air channels 226 (shown in phantom in FIG. 4) aligned with the vent opening 122 in lid 106. Thus, an air movement passage is created within the interior of diffuser 100 as indicated by air flow arrows 228, 230, and 232. This passage extends from front ventilation intake openings 148, past timing and indicating board 114 and heating element 112, through channels 226 of fragrance-emitting block 110, and out vent opening 122 to the ambient atmosphere.

The present invention contemplates that various models of diffuser 100 may be constructed for differing fragrance dispensing functions and fragrance output requirements, and that such models be equipped with differing heating element 112 having heat outputs or other characteristics as appropriate for the particular fragrance dispensing application for which the diffuser 100 is used. Accordingly, differing models of fragrance block 110 would be likewise constructed having the characteristics required for proper operation with a particular diffuser model.

A key plate 234 is removably attached in the rear portion of rear cover 104 and lies parallel to raised rear surface 164. Key plate 234 includes a plurality of key projections or tabs 236 extending forward therefrom to mate with corresponding key apertures or slots 238 (FIG. 8a) in fragrance block 110. Key tabs 236 are preferably arranged on key plate 234 in predetermined identification patterns associated with the particular type of heating element 112 or fragrance dispensing application for which the diffuser 100 is constructed. Fragrance block 110 preferably has a corresponding pattern of key slots 238 associated with the heater or fragrance dispensing application for which it was constructed. According to the invention, the key tabs 236 and fragrance block 110 would be cooperatively constructed to prohibit insertion into a particular diffuser 100 of a fragrance block 110 which does not have matching specifications. Details concerning the construction of the fragrance block 110, key plate 234, and key tabs 236 are shown in greater detail in FIGS. 8–15.

Figure 8:
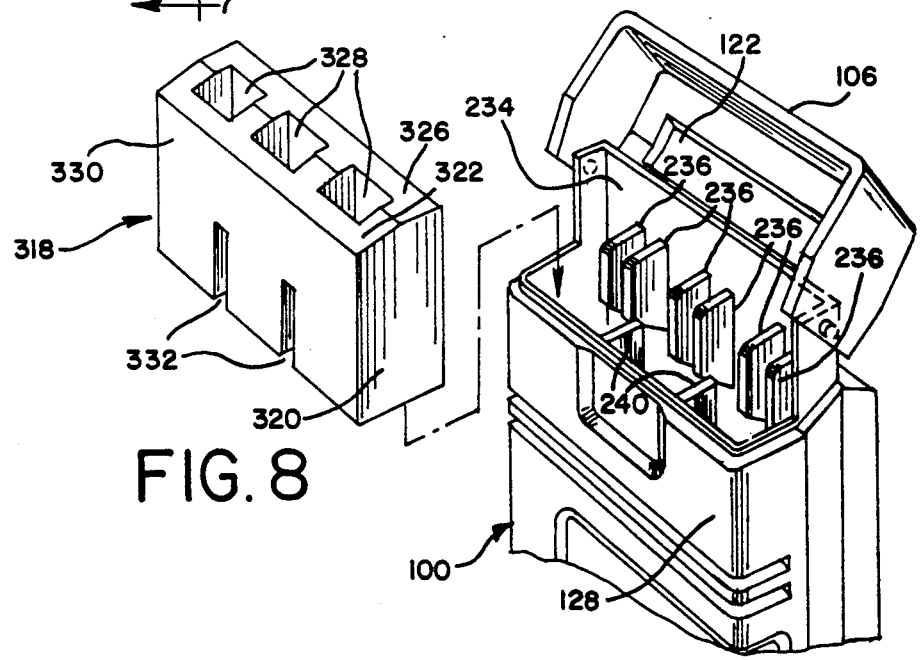
FIG. 8 is a perspective detailed view of the fragrance diffuser of FIG. 1 with its lid open, showing a fragrance block in position for insertion therein.

Two fragrance block alignment guides 240 preferably extend rearward from front wall 128 to ensure correct insertion of a fragrance block 110. Fragrance block 110 is constructed having mating alignment slots 332 (FIG. 8).

In operation, air is heated by heating element 112 (FIG. 4), and flows upward via convection through channels 226 in fragrance-emitting block 110, where it absorbs the fragrance impregnated therein. Heated, fragrance-laden air is discharged from vent opening 122 in lid 106. Ambient air is drawn inward through front ventilation intake openings 148 to replace the fragrance-laden air discharged from vent opening 122.

Figure 6:
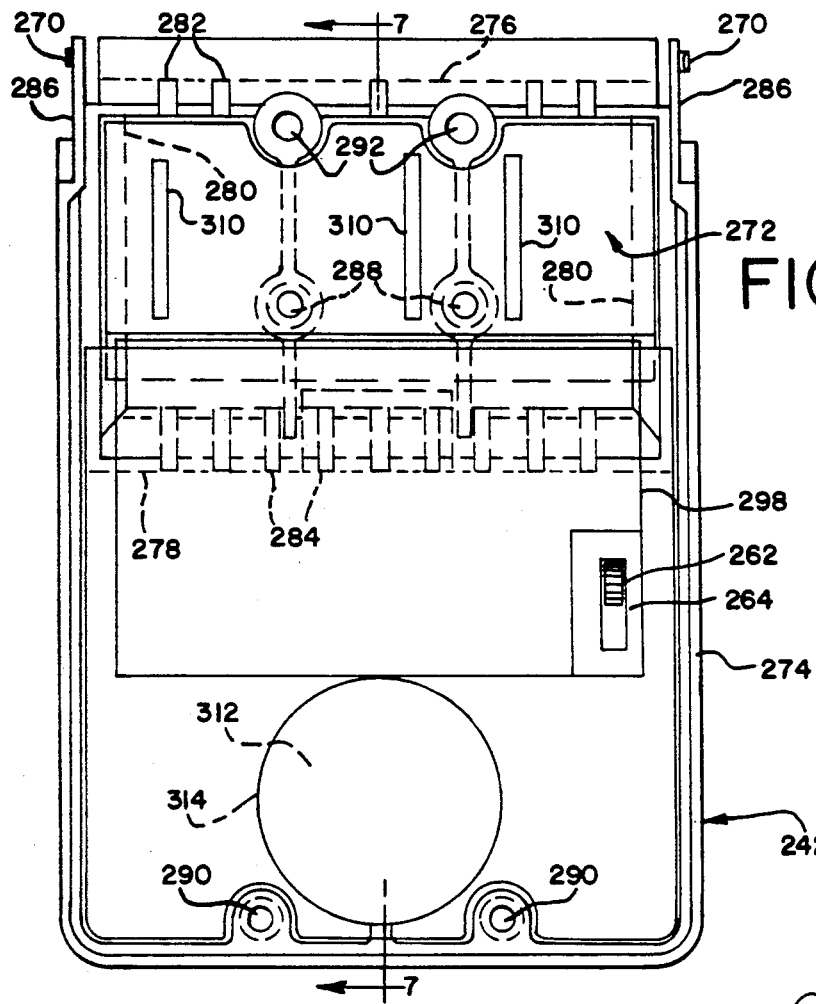
FIG. 6 is a front elevation view of a second embodiment of a fragrance diffuser according to the present invention in which the housing cover has been removed.

FIGS. 6 and 7, respectively, show a front view (with the cover removed) and a cross-sectional view of a second preferred embodiment of a fragrance diffuser according to the present invention. Diffuser 242 is generally similar to the previously disclosed diffuser 100 but lacks the indicators 156, 154, and switch actuator 152 of that embodiment. In addition, diffuser 242 has a simpler timing circuit, and the rotating plug is housed within the main portion of the diffuser 242, rather than in a lower projection as in diffuser 100. As a result, diffuser 242 is smaller and can be manufactured at lower cost, which may be advantageous in some applications.

Diffuser 242 includes a lid 244 (FIG. 7), a front cover 246, and a rear cover 248. These parts create an interior space including a region 250 for containing a fragrance-emitting block 252. Front cover 246 has upper and lower decorative striations 254, 256. The lower striations 256 preferably hide a plurality of slit-like horizontal ventilation openings 258 used for air intake. A front slot opening 260 permits an operating arm 262 of on-off switch 264 to extend through the front cover. The operating arm 262 is directly manually actuated by the user to supply or shut off electrical power to diffuser 242. A shallow depressed area 266 on the front cover 246 provides a location for operating arm 262 and appropriate labelling (not shown).

Lid 244 includes a vent hole 268 in its top surface and is attached for rotation to rear cover 248 using suitable pivot 270 (FIG. 6). Thus, lid 244 swings upward thereby providing the user access to region 250 for convenient installation and removal of fragrance emitting block 252.

Referring to FIG. 6, rear cover 246 includes an upper raised rear surface 272, side walls 274, and upper, lower, and side raised surface support walls 276, 278, and 280, respectively. A plurality of upper ventilation intake openings 282, and lower ventilation intake openings 284, which may be slots or holes, are provided in upper and lower raised surface support walls 278, 276, respectively, to permit ambient room air to enter the diffuser 242. As seen in FIG. 7, raised surface 272 provides additional room within the upper region 250 of the diffuser 242, and provides a predetermined ventilation clearance between the lower portion of the diffuser 242 and the wall surface (not shown) to which the diffuser is attached during normal use. Rear cover 246 has support tabs 286 on which pivot 270 are located for mounting lid 244. Holes 288 and 290 are provided in rear cover 248 for appropriate fasteners (not shown) for securing the rear cover 248 to the front cover 246. Holes 292 are also provided in rear cover 248 for fasteners 294 for securing the rear cover 248 to a vertical wall surface (not shown).

Heating element 296 resides beneath fragrance emitting block 252 and is controlled by control circuit 298. Control circuit 298 (FIG. 6) preferably includes printed circuit board 300 for providing electrical interconnection and physical support for the components thereof and for the heating element 296. Heating element 296 is attached using appropriate fastening and standoff means (not shown) to printed circuit board 300, a predetermined clearance being provided around heating element 296 for proper air circulation. Thermal insulator 302, which may be a flat mica sheet or other appropriate material, is preferably disposed via appropriate standoffs 304 between heating element 296 and front cover 246 to prevent damage to the material from which the cover is constructed. A similar insulator (not shown) may be provided to protect control circuit 298 from excessive heat.

Region 250 preferably includes fragrance block alignment guides 306, key plate 308, and key elements 310, which are constructed and which function as described for the analogous elements 240, 234, and 236 of diffuser 100, as shown in FIGS. 4 and 8.

Diffuser 242 also has a rotating power supply plug 312 mounted in an aperture 314 of rear cover 248, including insulating disk 254 and electrical plug contact members 316, which are constructed and function as described for the analogous elements 134, 200, and 206 of diffuser 100. Diffuser 242, however lacks a lower projection for housing rotating plug 312. Instead, rotating plug 312 is housed in the lower portion of the diffuser 242, which, as shown in FIG. 6, is substantially rectangularly shaped. Because the plug projection 196 of diffuser 100 is omitted, the diffuser 242 of the second preferred embodiment advantageously may be more compact, and may be constructed using less material, thereby reducing the cost of manufacture.

Figure 8A:
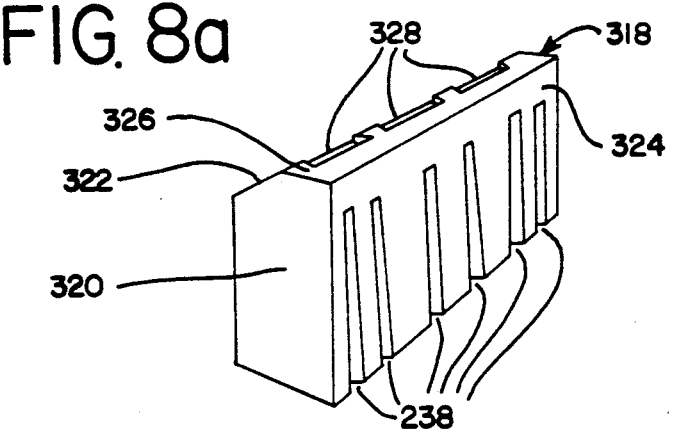
FIG. 8a is a different perspective view of the fragrance block of FIG. 8.

FIG. 8 shows a front perspective view of a fragrance-emitting block 318 according to the present invention in a suitable position pending insertion into one of the inventive diffusers 100, 242 of FIGS. 1 and 6, respectively. For convenience, diffuser 100 has been illustrated for this description, but with respect to the fragrance-emitting block 318, both diffusers 100, and 242 are preferably identical, and therefore this description applies equally well to diffuser 242. FIG. 8a shows a different perspective view of the fragrance-emitting block 318 FIG. 8, showing the rearward side of the block. FIGS. 9–14 illustrate the fragrance-emitting block 318 and key plate 234 in greater detail. FIGS. 9 and 10 show front and rear plan views of block 318, respectively. FIGS. 11 and 12 are cross-sectional views of block 318 taken across lines 11—11 and 12—12 of FIG. 9, respectively. FIG. 13 shows a front plan view of key plate 234. Finally, FIG. 14 shows a cross-sectional view of key plate 234 taken along line 14—14 of FIG. 13.

Referring to FIGS. 8 and 8a, fragrance-emitting block 318 is substantially a rectangular parallelepiped in shape and has substantially vertical side walls 320, a substantially vertical front wall 330, a substantially vertical rear wall 324, a horizontal bottom wall (not shown), a horizontal first upper surface 326, and a downwardly-angled second upper surface 322. The fragrance-emitting block 318 is preferably fabricated from a porous plastic material, and an appropriate fragrance-bearing media is impregnated therein.

A plurality of hollow air channels 328 are provided extending vertically through the block 318 from the bottom wall to the upper surfaces 326, 322. Air channels 328 are preferably disposed within fragrance-emitting block 318 such that when block 318 is inserted into the diffuser 100, the channels 328 receive a substantial portion of the air flowing upward from heating element 112. Thus, fragrance impregnated in the block 318 diffuses primarily into the air passing through channels 328.

In the preferred embodiment of fragrance-emitting block 318 illustrated in FIG. 8, three air channels 328 of the rectangular cross-section are shown, providing an acceptable tradeoff between the ease of manufacturing block 318 and the efficiency of fragrance diffusion within the channels 328. Other cross-sections or a different number of channels may be preferred where necessary to increase or decrease the surface area thereof, thereby affecting the efficiency of fragrance diffusion. The preferable configuration of air channels 328 may depend on the particular fragrance-bearing media impregnated in the block 318 and the temperature of air supplied by heating element 112.

Front wall 330 includes two alignment slots 332 extending vertically from the bottom wall for a distance of approximately one half the height of the block 318. Alignment slots 332 engage mating alignment guides 240 extending inward from diffuser front cover 102 to ensure correct orientation of the block 318 upon insertion into the diffuser.

Rear wall 324 (FIG. 8a) includes a plurality of key slots 238 in predefined positions extending vertically from the bottom wall for a distance of approximately three quarters the height of the block 318. Key slots 238 engage mating key tab 236 extending inward from key plate 234 to prevent incorrect fragrance-emitting blocks 318 from being inserted in the diffuser 100. Key plate 234 is removably mounted parallel to the diffuser rear cover 104 using suitable fastening means (not shown).

Key plate 234 has a substantially rectangularly shaped plate member 334 on which key tabs 236 are mounted (FIGS. 13, 14). When key plate 234 is installed in diffuser 100, it lies parallel to the raised rear surface 164 of rear cover 104. A ledge member 336 extends horizontally inward from plate member 334 and provides a resting position for fragrance-emitting block 318. A vertical lip 338 extends downward from ledge member 336 a short distance inward from plate member 334. Apertures 340 in plate member 334 are provided for mounting the key plate 234 to the diffuser rear cover 104 using suitable fastening means (not shown). U-shaped openings 342 (FIG. 13) in the upper edge of key plate 334 provide clearance for fasteners 294 (FIG. 7) used to secure the diffuser to a room wall surface (not shown). Standoffs 344 (FIGS. 13, 14), which are slightly raised vertical ridges, provide a guaranteed clearance between the fragrance-emitting block 318 and the plate member 334. Angled upper surfaces 346 on standoffs 344 prevent the block 318 from catching on the standoffs 344 during insertion.

Key plate 234 preferably includes a particular predefined identification pattern of key tabs 236 identifying the characteristics (e.g. heater temperature) of the diffuser 100 in which it is installed. Key tabs 236 extend outward from key plate 234 to prevent insertion of any block 318 which does not have key slots 238 in at least all of the positions corresponding to key tabs 236. A particular set of diffuser characteristics would be associated with a unique key pattern, and a key plate 234 bearing that pattern of key tabs would be installed in diffusers having that set of characteristics. Only fragrance-emitting blocks 318 suitable for use with those pre-established diffuser characteristics would be manufactured with key slots 238 in that pattern, and thus only matching blocks 318 could be successfully inserted in the diffuser.

A preferred embodiment of a key pattern scheme according to the present invention is illustrated in FIGS. 8–15 in conjunction with Table 1 below. A total of six key positions 348a–348f (FIG. 13) are defined on key plate 234 and fragrance-emitting block 318 (FIGS. 9, 10). The key positions are divided into three groups of two key positions each: Group I, comprising key positions 348a and 348b; Group II, comprising key positions 348c and 348d; and Group III, comprising key positions 348e and 348f. A key position is considered "occupied" where, on a block 318, a corresponding key slot 350a–350f (FIG. 10) is present, or, on a key plate, a corresponding key tab 352a–352f is present in that position. To best illustrate the correspondence of the key positions 348a–348f, key slots 350a–350f, and key tabs 352a–352f, all six possible positions are shown as occupied in FIGS. 8–14. However, using the preferred key scheme discussed below, an actual block 318 and matching key plate 234 would have only three positions occupied.

Under the preferred key scheme, one of the key positions in each of the three groups is always occupied, and the remaining key position in each of the three groups is always unoccupied. This results in eight possible combinations of key positions, corresponding to eight possible diffuser types, as shown in Table 1 below. For each of the eight combinations, Table 1 indicates which of the two key positions in each of the three groups are occupied. An 'X' in the key position column indicates that the position is occupied, and a blank in that column indicates that the position is unoccupied.

TABLE 1

| Diffuser Type | Key Positions | | | | | |
|---|---|---|---|---|---|---|
| | Group I | | Group II | | Group III | |
| | 348a | 348b | 348c | 348d | 348e | 348f |
| 1 | X | | X | | X | |
| 2 | X | | X | | | X |
| 3 | X | | | X | X | |
| 4 | X | | | X | | X |
| 5 | | X | X | | X | |
| 6 | | X | X | | | X |
| 7 | | X | | X | X | |
| 8 | | X | | X | | X |

Figure 15A:
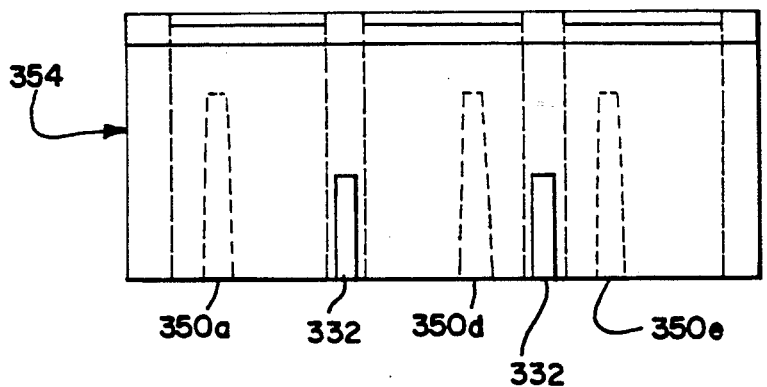
FIG. 15a is a front plan view of a fragrance block constructed according to the preferred key scheme of the present invention.
Figure 15B:
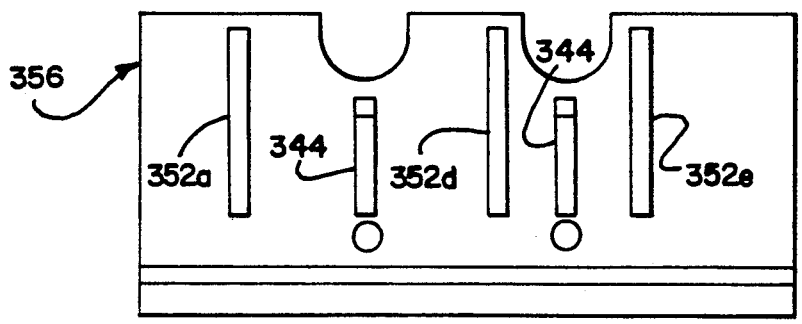
FIG. 15b is a front plan view of a key plate constructed according to the preferred key scheme of the present invention.

FIG. 15a shows a front plan view of a fragrance-emitting block 354 complying with one embodiment of the above-described key scheme, corresponding to diffuser type 3 in Table 1. FIG. 15b shows a front plan view of a matching key plate 356 according to the same key scheme. As shown in Table 1, diffuser type 3 requires that key positions 348a, 348d, and 348e are occupied. Therefore, block 354 includes key slots 350a, 350d, and 350e, and key plate 356 has key tabs 352a, 352d, and 352e, as shown. Key slots and key tabs are not present at key positions 348b, 348c, and 348f. If key plate 356 were installed in diffuser 100, block 354 could be properly inserted because key slots 350a, 350d, and 350e coincide with key tabs 352a, 352d, and 352e.

It can be seen by examining Table 1 that a fragrance-emitting block keyed for any diffuser type other than diffuser type 3 in the above example could not be inserted, because key plate 356 would have at least one key tab 352 in a key position for which there is no matching slot in that block. For example, a block keyed for diffuser type 4 lacks a slot in position 348e, and therefore would be blocked from insertion into a type 3 diffuser by key tab 352e. Hence, if all key plates and fragrance-emitting blocks are manufactured according to this scheme, only fragrance-emitting blocks matching a diffuser's particular key plate can be successfully inserted in that diffuser.

While a preferred embodiment of a key scheme has been described, other key schemes could employ the disclosed mechanical structures with advantageous results. If a larger number of diffuser types is desired, the number of groups of key positions, or the number of key positions within each group, may be increased. For example, three groups of three key positions would provide 27 key combinations. Four groups of two key positions would provide 16 key combinations. If a smaller number of diffuser types is desired, a unique key position might be associated with each diffuser type.

Moreover, individual key positions might be associated with particular diffuser attributes. For example, if a particular diffuser was constructed with a high temperature heater and therefore required a fragrance-emitting block adapted for operation at high-temperature, a unique key position might be associated with a high-temperature-heater attribute. The key plate would include a key tab in that position, and only blocks having a matching key slot (presumably, only blocks adapted for high-temperature operation) could be inserted in that diffuser. Under such a scheme, blocks having several attribute key slots may be manufactured, and any block which has at least those attribute key slots represented by a diffuser's key plate could be inserted therein.

In addition, while the preferred key scheme has been heretofore described primarily as a means of ensuring that only fragrance-emitting blocks adapted for operation with a particular diffuser be insertable in that diffuser, the key scheme may be employed to associate certain fragrance-emitting blocks with certain diffusers for other purposes. For example, the operator of a hotel may desire that guest rooms primarily occupied by non-smoking guests receive a different fragrance than rooms occupied by smoking guests. The fragrance-emitting blocks may be keyed according to the particular fragrance, or strength of fragrance, they emit. The diffuser in each guest room could then be equipped with a key plate permitting insertion of only fragrance-emitting blocks bearing the fragrance or strength selected for that room.

Referring now to FIGS. 16 and 17, the construction of rotating plug 134 is shown in greater detail. For convenience, diffuser 100 has been illustrated for this discussion, but with respect to the rotating plug 134, both diffusers 100 and 242 are preferably identical (except where noted), and therefore this discussion applies equally well to diffuser 242. FIG. 16 is a plan view of plug 134 from the front of diffuser 100 with its cover off. FIG. 17 is a side elevation view of the plug 134 as it would appear prior to assembly in diffuser 100.

Disk 200 is a substantially circular disk preferably constructed of an electrically insulating plastic. Plug blades 206, 208 are preferably constructed of an appropriate stiff, electrically conductive metal, such as brass. Plug blades 206, 208 are connected via flexible wires (not shown) secured by fasteners 210, 212 to the timing circuit 114 to supply power thereto. Disk 200 has a circular outer portion 358 which, when assembled, fits into a circular hole 202 (FIG. 4) in the rear cover 104 of diffuser 100. A lip 360 of a slightly larger diameter than outer portion 358 encircles outer portion 358 to capture disk 200 within the diffuser 100. When assembled, the rear surface of lip 360 thus engages the front surface of guide 202 (FIG. 4) of the rear cover 104. A guide 204 on the front cover 102 similarly engages the front surface of lip 360 and an intermediate raised surface 362 on the front surface of disk 200 to maintain disk 200 in position against the rear cover 104.

Within guides 204, and 202, disk 200 is free to rotate. However, stop tab 364 (FIG. 4), which extends toward intermediate raised surface 362 from front cover 102, and raised limit surface 366 cooperate to limit the total possible rotation travel of disk 200 to approximately 180 degrees. As disk 200 is rotated toward a limit of travel, raised limit surface 366 approaches and engages stop tab 364, thereby preventing further rotation. This is necessary to avoid applying excessive stress to the electrical connecting wires.

V-shaped grooves 368, 370, and 372 are preferably located at 90 degree intervals in the rear surface of lip 360 and engage a mating knob (not shown) on the rear surface of guide 202. This action provides a tactile response to the operator when rotating the plug 134 to identify predefined positions when the plug orientation is either horizontal or vertical. In addition, once rotated to one of the predefined positions, this mating of the groove and knob retains the plug in that position unless forcibly displaced by the operator, thereby easing installation.

Figure 18:
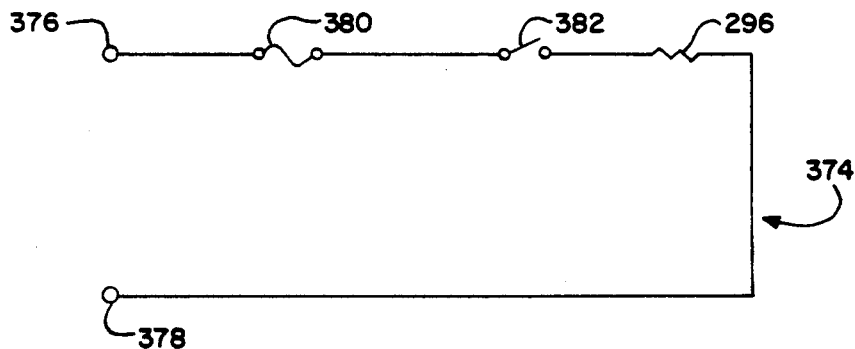
FIG. 18 is an electrical schematic diagram of an appropriate heater power circuit for the diffuser embodiment of FIG. 6.

FIG. 18 shows an electrical schematic diagram of a heater circuit for the second embodiment 242 (FIG. 6) of a fragrance diffuser according to the present invention. Circuit 374 comprises power supply terminals 376, 378, fuse 380, heater operating switch 382, and heating element 296 connected in series. Fuse 380 is preferably a thermal fuse which will open if a short-circuit develops or if the temperature inside the diffuser housing exceeds a predetermined level. Power supply terminals 376, 378 are preferably connected by electrical wires (not shown) to power supply plug 312.

Figure 19:
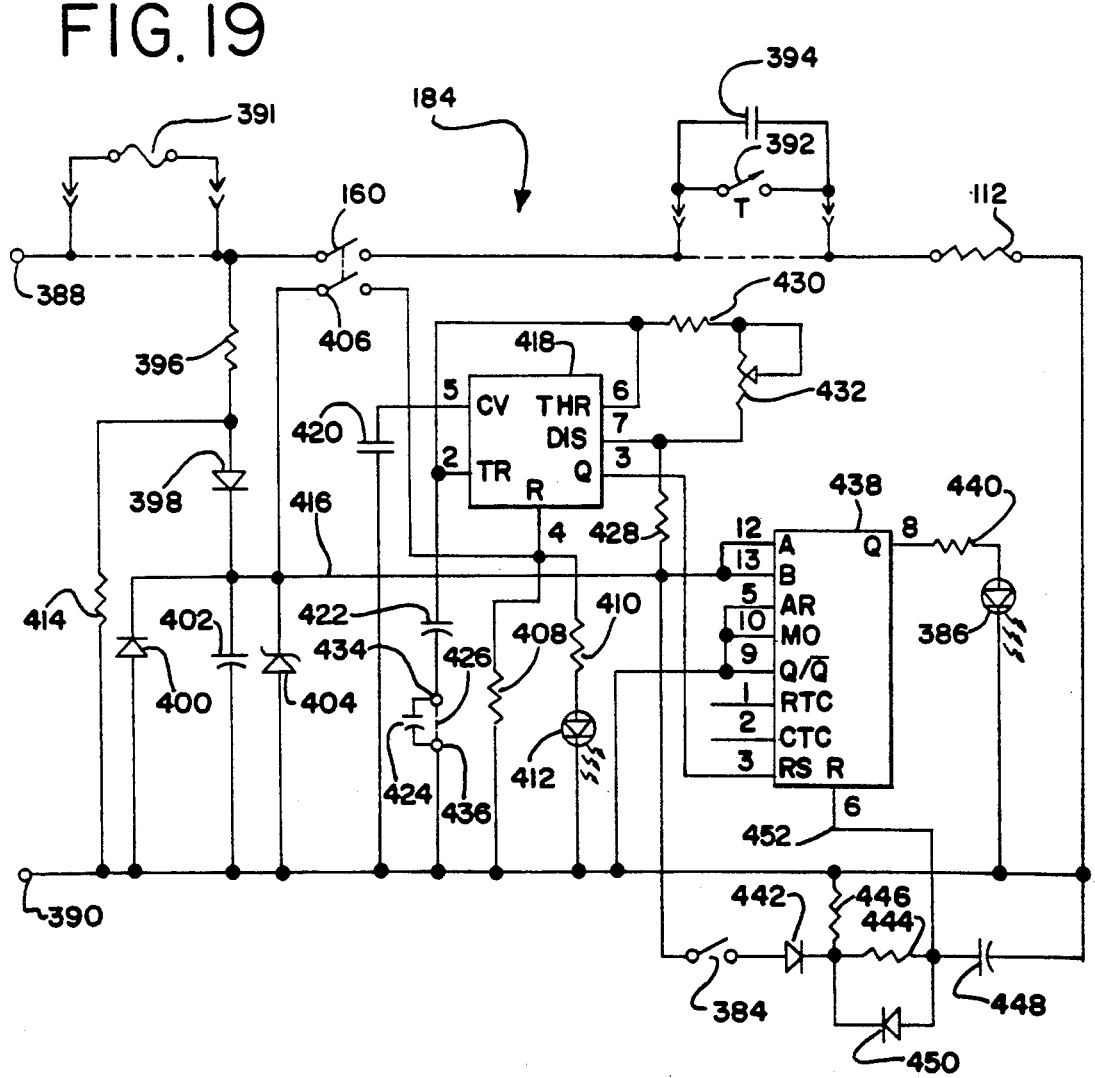
FIG. 19 is an electrical schematic diagram of appropriate heater power, timer, and indicator circuits for the diffuser embodiment of FIG. 1.

FIG. 19 shows an electrical schematic diagram of a heater timing and indicator circuit 184 for the first embodiment 100 (FIG. 1) of a fragrance diffuser according to the present invention. Circuit 184 provides an indication that a predefined diffuser operating period, which preferably corresponds to the approximately 30-day lifetime of a fragrance-emitting block, has expired. The circuit 184 begins measuring this period from the time the heater receives power (i.e. the diffuser is plugged into an active electrical outlet and operating switch 160 is switched to the "on" position) or from the operation of the reset switch 384. After the predefined timing period has expired, visual indicator 386 lights to notify a user that replacement of the fragrance emitting block 110 may be required. Visual indicator 386 remains lit until power is removed from the device, the operating switch 160 is turned "off", or the reset switch 384 is operated by a user.

In contrast to the prior art, expiration of the timing period has no effect on operation of the heating element 112. Since diffuser 100 includes a relatively low-temperature heating element 112, continuous operation beyond the expected lifetime of the fragrance block 110 has no detrimental effect. In addition, because the fragrance block 110 typically still contains some fragrance-bearing media, continued heater operation may provide effective room air treatment until the user notices the indicator and replaces the expended block.

The configuration of heater timing and indicator circuit 184 will be best understood by dividing the circuit into a number of subsections. A heater operating subsection provides switched line-voltage power to heating element 112. An oscillator subsection provides a stable source of timing pulses for timing interval measurement. A counter subsection counts a specified number of timing pulses and illuminates indicator 386 when a predetermined period of operation has elapsed. A reset subsection resets the timing subsection under particular conditions. A low voltage power supply subsection provides appropriate low voltage power to the oscillator, counter, and reset subsections. In the discussion below, component values and types given in parenthesis are examples of values and types known to be suitable, although other values and component types may also be appropriate.

The heater operating subsection comprises a portion of operating switch 160 and heating element 112, connected in series. This subsection obtains power from hot and neutral power supply terminals 388, 390 respectively, which are connected by wires (not shown) to prongs 206, 208 of rotating power supply plug 134. A thermal fuse 391 or other appropriate protective device may be inserted in series if required for government or private laboratory approval, or to meet other safety considerations. If a heater is used which provides a higher temperature than required for proper operation, a thermostat 392 may also be inserted in series with heating element 112 to disable the heating element when the desired temperature is exceeded. A capacitor 394 is preferably provided in parallel with thermostat 392 to minimize electromagnetic interference and other undesirable effects which may occur when thermostat 392 opens and closes. If a low temperature heating element is used, a thermostat may not be necessary.

The power supply subsection comprises a resistor 396 (5.6 k, 3w), a pair of rectifiers 398, 400 (type 1N4004), a capacitor 402 (100 uF, 25 V), a Zener diode 404 (type 1N4741, 11.0 V), the second pole 406 of the operating switch, a bias resistor 408 (4.7 k), a current-limiting resistor 410 (10 k), and a light-emitting diode (LED) indicator 412. This subsection also obtains power from hot and neutral power supply terminals 388, 390, respectively, which are connected by wires (not shown) to prongs 206, 208 of rotating power supply plug 134. Diffuser 100 is normally plugged into a 120 VAC electrical outlet. Resistors 396 and 414 serve as a voltage divider and current limiter to provide an appropriate input level to rectifiers 398, 400. Rectifiers 398, 400 are connected in a half-wave rectifying configuration to convert the AC input to pulsating DC. The neutral AC input connection 390 serves as the power supply negative output lead, and is hereinafter referred to as "ground". Signal lead 416 is the rectifier positive output lead and is hereinafter referred to as "V+". Capacitor 402 filters ripple from the power supply output. Zener diode 404 is connected from V+ 416 to ground 390 to regulate the output voltage of the power supply subsection at 11.0 VDC.

Operating switch second pole 406 controls power-on LED indicator 412. When switch 406 is closed, V+ 416 is connected to dropping resistor 410, and current may flow to illuminate LED indicator 412. Dropping resistor 410 limits current through LED indicator 412 to about 1 mA. An incandescent lamp or other appropriate indicating device could also be used. When operating switch second pole 406 is closed, V+ 416 is also connected to the active-low reset input of oscillator integrated switch 418, permitting that device to operate. When the switch is open, pull-down resistor 408 pulls the reset input to ground 390, inhibiting operation of oscillator 418.

The oscillator subsection comprises an oscillator IC 418, which is preferably a type 7555 CMOS timer. This device is well known to those skilled in the art, and is available from Intersil and several other suppliers. The oscillator subsection further comprises capacitors 420 (0.01 uF), 422 (20 uF, 20 V), and optionally 424 (220 pF), removable jumper 426, resistors 428 (4.7 K) and 430 (1 M), and variable resistor 432 (2 M). These capacitors and resistors control the frequency and other operating parameters of the oscillator device 418.

In particular, the output frequency of oscillator IC 418 is largely controlled by resistors 430, 432, capacitors 422, 424, and the presence of jumper 426. Fine adjustment of the oscillator may be performed by adjusting variable resistor 432. In normal use, jumper 426 is installed across terminals 434 and 436, thereby shorting capacitor 424 and providing an oscillator output frequency of approximately 0.01375 Hz.

The pulses from output Q of oscillator IC 418 are counted by counter IC 438 of the counter subsection (discussed below in greater detail). When counter IC 438 has received 32767 pulses, it illuminates block replacement LED indicator 386. This occurs after a timing interval of approximately 30 days. If other timing periods are desired, the values of resistors 430 and 432, and/or capacitor 422, may be varied to provide an appropriate time constant, thereby determining the output frequency of oscillator IC 418. In addition, jumper 426 may be removed to provide a convenient test mode, multiplying the output frequency of oscillator IC 418 by approximately 100,000 by placing capacitor 424 in series with capacitor 422. This produces an output frequency of approximately 1250 Hz, triggering block replacement indicator 386 in approximately 26 seconds. This permits more convenient testing during manufacturing, since resistor 432 may be readjusted and the circuit retested in a short time.

The counter subsection comprises counter integrated circuit 438, dropping resistor 440, and block replacement LED indicator 386. Counter IC 438 is preferably a multistage output-addressable binary counter available from Motorola (type MC14541) or Signetics (type HEF4541) or other suppliers. Counter IC 438 receives and counts clock pulses received at its clock input (pin 3) from the Q output of oscillator IC 418, and when a predetermined number of clock pulses have been received, it provides drive current to operate LED indicator 386. The mode select, auto-reset, and output polarity inputs (pins 10, 5, and 9, respectively) are preferably connected to ground 390, thus enabling the automatic reset, single-cycle, and normal output polarity modes of the counter. The A and B address inputs (pins 12 and 13) of counter IC 438 are preferably connected to V+ 416 to place counter IC 438 in its divide-by-65536 mode.

In the single-cycle divide-by-65536 mode, the output of counter IC 438 remains low from the time power is applied to the device, or a reset operation has occurred, until the counter IC 438 has received 32,767 pulses. When this occurs, the Q output of counter IC 438 is driven high, supplying current through dropping resistor 440 to LED indicator 386. Since oscillator IC 418 provides clock pulses at approximately 0.01375 Hz, this counting mode results in a clock period of about 2.4 million seconds or about 30 days. If other clock periods are desired, either the pulse frequency of oscillator IC 418 may be changed as described above, or the counting parameters of counter IC 438 may be changed.

Indicator 386 is preferably a light-emitting diode, but other devices which do not require excessive drive current (relative to the output of counter IC 438) could also be used. Dropping resistor 440 is preferably a 10 K-Ohm resistor, which limits the drive current supplied to LED indicator 386 to about 1 mA.

The reset subsection permits the user to reset counter IC 438, thereby starting a new timing period and extinguishing LED indicator 386 (if that indicator is lit), by operating reset switch 384. In order to prevent resetting of the timing period due to accidental bumping of reset switch 384, the reset subsection is designed to require that the reset switch be held closed for approximately two seconds before it actually resets counter IC 438. The reset subsection comprises reset switch 384, protection diode 442 (type 1N4148), timing resistor 444 (100 K), bleeder resistor 446 (10 K), timing capacitor 448 (20 uF), and bleeder diode 450. The output signal 452 from the reset subsection is provided from the non-grounded terminal of capacitor 448 to the reset input (pin 6) of counter IC 438.

In its normal state (i.e. with power applied to the circuit and the reset switch 384 open), the output signal 452 of the reset subsection is low (approximately 0 V). Starting from that state, operation (i.e. closure) of momentary reset switch 384 effectively connects V+ to the anode of diode 442, permitting current to flow through resistor 444 to charge capacitor 448. Diode 450 is reverse-biased such that it and resistor 446 have a negligible effect on the circuit while reset switch 384 is closed. The time constant of the circuit during charging is approximately 2 seconds, as determined by the preferred values of resistor 444 100 K) and capacitor 448 (20 uF). The voltage at the non-grounded terminal of capacitor 448 is presented to the reset input (pin 6) of counter IC 438 via signal 452. When the reset switch has been held closed for about 2 seconds, capacitor 444 will have charged to about seventy percent of the V+ voltage, thus triggering the reset input R of counter IC 438.

When reset switch 384 is opened, the large positive voltage at capacitor 448 forward-biases diode 450, permitting capacitor 448 to discharge through that diode and resistor 446 to ground 390. Since resistor 444 is shunted by diode 450, the time constant during discharge is determined by the values of resistor 446 (10 K) and capacitor 448 (20 uF) which is about 0.2 seconds. Thus, capacitor 448 discharges comparatively rapidly. If the reset switch is held closed only briefly (i.e., shorter than the required two-second charging time constant), capacitor 448 will fail to charge to a sufficient level to activate the reset input of counter IC 438, and that device will not be reset. This provides protection from accidental resets due to accidental bumping of the reset switch or similar events.

In operation, when power is applied to the diffuser, the power supply subsection provides power to oscillator IC 418, counter IC 438, and related components. Counter IC 438 is initially reset, and block replacement LED indicator 386 is extinguished. When operating switch 160 is in the "off" position, no power is supplied to heating element 112, and oscillator IC 418 is inhibited from producing clock pulses to counter IC 438. When operating switch 160 is switched to the "on" position, operating power is supplied to heating element 112. V+ 416 is then provided to power-on indicator 412 and to oscillator IC 418, permitting oscillator IC 418 to produce clock pulses for counter IC 438, in turn allowing counter IC 438 to accumulate elapsed time. When counter IC 438 has accumulated approximately 30 days of elapsed heater operating time (or any other selected period), counter IC 438 enables block replacement LED indicator 386. When reset switch 384 is operated for at least two seconds, counter IC 438 is reset, extinguishing LED indicator 386 and starting a new timing period.

Thus, a fragrance diffuser has been disclosed which overcomes a number of the disadvantages of the prior art. The diffuser incorporates a keying system to permit the insertion of only appropriately-designed fragrance-emitting blocks into its heated diffusing chamber. The blocks may be encoded to indicate that they possess individual characteristics, so that only blocks having those characteristics may be inserted. The diffuser comprises a low-temperature heating element to provide a substantially consistent level of aroma diffusion. The diffuser is constructed with a downwardly-protruding housing extension for the power supply connection, to allow the use of an adjacent electric power outlet when the diffuser is properly installed. The diffuser also includes circuitry to indicate when a timing interval, corresponding to the life of a fragrance block inserted therein, has expired, wherein the timing interval is restarted only at the request of a user.

Figure 20:
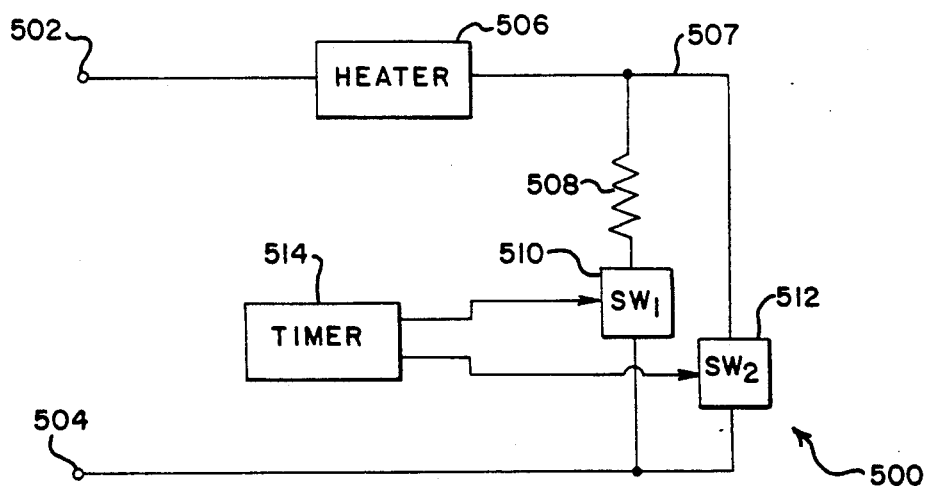
FIG. 20 is an electrical block diagram of an alternate heater power circuit which provides a stepped heating for the fragrance diffuser in accordance with the present invention.

Referring now to FIG. 20, an alternate embodiment of a heater power circuit for a fragrance diffuser is shown in block diagram form. Heater circuit 500 of FIG. 20 can be used with any of the fragrance diffuser embodiments described above. Heater circuit 500 provides the diffuser with a multi-level or "stepped" heating capability which is designed to vary the power applied to the heating element over the lifetime of the fragrance-emitting block. In the embodiment shown in circuit 500, stepped heating is accomplished by switching in or out a resistor in series with the heating element, thus reducing the power dissipation of the heating element. In the preferred embodiment of the stepped heating system, which will be described in detail in FIG. 23, the duty cycle for the operation of the heater is also used to accomplish the same result.

More specifically, circuit 500 comprises power supply terminals 502, 504, which are connected by wires (not shown) to prongs 206, 208 of rotating power supply plug 134 as described above. If desired, a thermal fuse or other appropriate protective device may also be inserted in series. One terminal of heating element 506 is connected directly to the power supply terminal 502, while its other terminal at node 507 is connected via a first or second switching path to power supply terminal 504. In the first switching path, a resistor 508 is connected in series with a first switching device 510. If switch 510 is turned on, then electric power will be applied to heating element 506 through resistor 508 at a reduced voltage and current level. In the second path, a second switching device 512 is connected directly from node 507 to terminal 504. If switch 512 is turned on, then heating element 506 will be connected directly across the power supply terminals 502, 504, without having its voltage or current limited by a supplementary resistor.

Timer circuit 514 controls both switching devices 510, 512. The timer circuit starts measuring time after the reset switch is pressed, and provides at least one timer output signal indicating when a predefined period of time has expired. This predefined period of time would correspond to the time when the power applied to the heating element should be changed, which is typically a fraction of the useful life of a fragrance block. For example, in a fragrance block having a useful life of approximately 30 days, then the initial time period, for which a low power should be used, might correspond to one week. Depending upon how the timer circuit is configured, the power could be increased again after a second week has lapsed after the installation of a new fragrance block. Hence, the average power applied the heating element 506 can be stepped in two- or three-level increments, or could even be continuously varied.

Using the above time periods with heater circuit 500, timer 514 would provide a first output signal to activate only switch 510 during the initial 7 day period when the fragrance block is at full strength, while switch 512 was turned off. This configuration would apply a reduced amount of voltage and current, and thus reduced power, to heating element 506, while the remaining power is dissipated by resistor 508. After 7 days, timer 514 would turn on switch 512, such that full power is applied to heating element 506. If switch 512 was on, it would not matter whether or not switch 510 was on. Hence, this would provide a two-level heating system.

Essentially the same circuit 500 can be used to provide a three-level heating system, simply by altering the duty cycle of at least one of the output signals provided by timer 514. This will be explained in greater in detail in accordance with FIG. 23. Note that in FIG. 20, switch 510 is optional. If switch 510 were replaced with a short circuit, then a single switch 512 would produce a two-level heating system. However, the use of both switches 510, 512 allows the timing circuit 514 to turn the heating element 506 off after a period of time. It should further be noted that a multi-level heating system could readily be made by adding parallel resistor/-switching device paths between node 507 and terminal 504. In that case, the current through heating element 506 would be varied by switching in different resistors having different values.

Note also that either switching device 510, 512 could be implemented by a relay, a silicon controlled rectifier (SCR), a triac, or similar 120 VAC switching device. Note that if a triac is used for switching device 512, then a diode could be used in place of resistor 508. This would produce a two-level heating system, wherein the low-power path through the diode would apply half-wave AC voltage to heating element 506, while the high-power path through the triac would produce full-wave voltage to the heating element. The same result would be accomplished if switch 510 was an SCR, while switch 512 was a triac.

Figure 21:
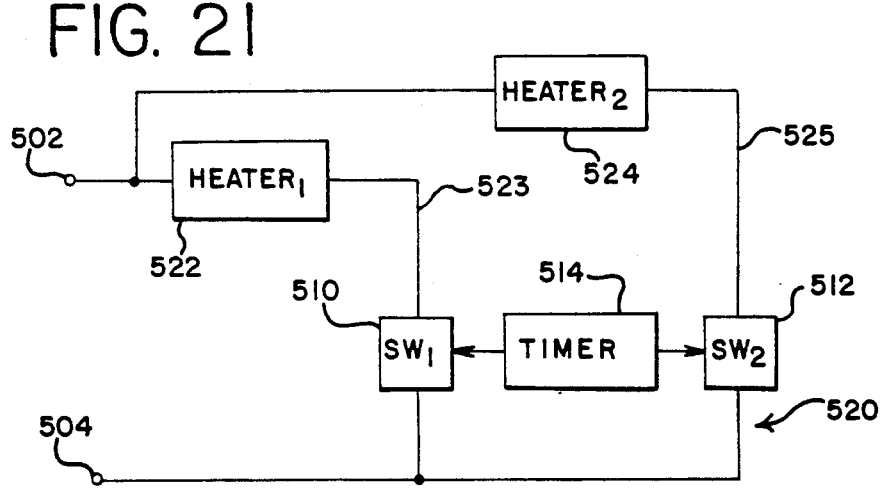
FIG. 21 is an electrical block diagram of another embodiment of a heater power circuit in accordance with the present invention.

FIG. 21 illustrates an alternative embodiment of a two- or a three-level heater power circuit 520. In this embodiment, two heating elements are used, wherein one or both of the heating elements are switched into the circuit to produce the different heating levels. In circuit 520, a first heating element 522 is connected in parallel with a second heating element 524 as shown. A first switching device 510 is connected in series with heating element 522 to couple node 523 to the second power supply terminal 504. The second switching device 512 is connected to node 525 to couple the second heating element 524 to the second power supply terminal 504. As before, timer circuit 514 is configured to control both switching devices.

In heater power circuit 520, one or both heating elements are switched into the circuit to produce the different heating levels. For example, for the first 7 days, only switch 510 would be activated to turn on heating element 522. After 7 days, timer 514 would also activate switch 512 to apply power to heating element 524. This would produce a two-level heating system. If heating element 522 was constructed to have a different heating (or wattage) rating, then a three-level heating system would be configured. For example, if heating element 522 had a low power rating, then only switch 510 would be on for the first 7 days. From 7 to 15 days, heating element 524, having a medium power rating would be activated by switch 512 while switch 510 was off. Finally, after 15 days, both heating elements 522, 524 would be on to produce a high power rating in combination. Again note that switch 510 is optional, since if heating element 522 were always on, i.e., node 523 connected to terminal 504, then heating element 524 would be switched in or out by switching device 512, thereby providing a two-level heating system.

Figure 22:
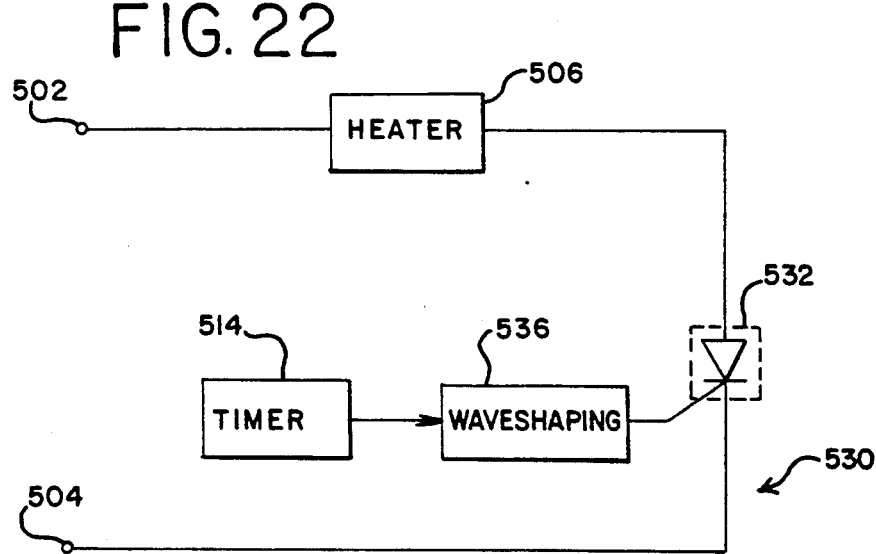
FIG. 22 is an electrical block diagram of still another heater power circuit in accordance with the present invention.

FIG. 22 illustrates a block diagram of still a further embodiment of the present invention, wherein a single heating element 506 is connected in series with a single switching device 532 as shown. However, in circuit 530, timer circuit 514 provides a timing signal to a waveshaping circuit 536 that controls the switch 532. Although switch 532 is illustrated as an SCR in the figure, other types of switches could readily be used.

At least two waveshaping techniques could be used to provide varying power levels to heating element 506. In the first type, the duty cycle of the control signal applied to switch 532 would be varied, such that power increases as time lapses. For example, timer 514 would produce an output timing signal every 7 days to waveshaping circuit 536. The waveshaping circuit would output a waveform having a duty cycle that increases in accordance with the timing signal. For example, switch control signal having a 50% duty cycle would be produced for the first 7 days i.e., 30 minutes, on 30 minutes off. After 7 days, waveshaping circuit 536 would change the duty cycle to 75%, i.e., 30 minutes on, 10 minutes off. After 15 days, the duty cycle would be changed to 100%, i.e., constantly on. If desired, after 30 days, switching device 532 could be turned off. Electronic timing and waveshaping circuitry for performing this type of duty cycle alteration will be described in accordance with the following figures.

The second technique for varying the power level in the circuit of FIG. 22 would be to control the conduction angle of switching device 532. According to the principles of phase control, the conduction angle is the period of time during the AC cycle in which the AC switching device is conducting. Conduction angle is measured in electrical degrees. Such phase control techniques could be used with either an SCR or a triac. Phase control for SCR and triac switches is well-known in the art. For more information, refer to Motorola Applications Note AN-240, entitled "SCR Power Control Fundamentals," Motorola Semiconductor Products Inc., Phoenix, Ariz., 1971. Note that if a triac were used for switching device 532, then a simplified two-level heating system would be provided if waveshaping circuit 536 included a diode in series with the gate terminal of the triac, and the diode was switched in or out of the gate circuit in response to a signal from timer circuit 514.

Figure 23:
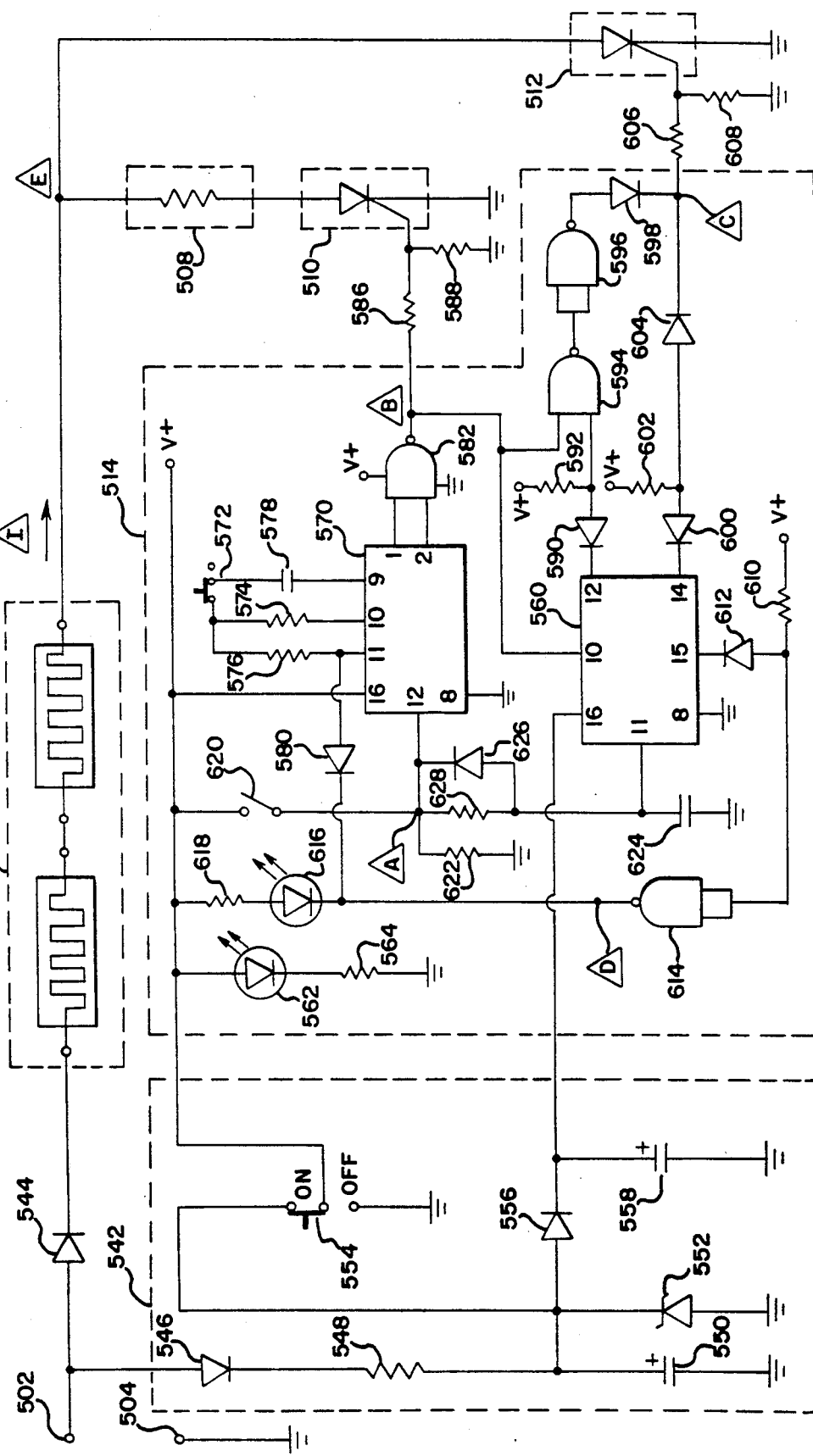
FIG. 23 is a detailed electrical schematic diagram of one implementation for the heater power circuit of FIG. 20.

Referring now to FIG. 23, a detailed electrical schematic diagram of circuit 540 is shown, which corresponds generally to the block diagram of FIG. 20. AC power terminals 502, 504 are illustrated on the left side of the figure. These terminals represent the source of AC power at 120 VAC at 60 Hertz. A power supply subsection 542 is used to provide DC voltage for the timer circuit 514. A diode rectifier 544 (type 1N4004), in series with the AC power line to the heating element 506, provides half-wave rectification of the AC waveform to avoid overheating caused by any short circuit of either of the SCR switching devices 510 or 512 (type 2N5064. Resistor 508 (150 ohm, 1 watt) serves the function of reducing the power to the heating element 506 when only switch 510 is on.

In the DC power subsection 542, a diode rectifier 546 (type 1N4004) provides half-wave rectified voltage to a resistor 548 (10 K, 3 watt), a capacitor 550 (100 uF), and a Zener diode 552 (type 1N5239, 9.1 V). These components provide 9.1 volts DC at V+ when the on/off switch 554 is in the "on" position. A yellow light emitting diode (LED) 562, connected in series with a resistor 564 (2.7 K), provides an indication of when power is supplied to the diffuser via the on/off switch. Another diode rectifier 556 (type 1N4004) and a capacitor 558 (100 uF), provide a constant power source to maintain the output state of a counter IC 560 for at least six hours when on/off switch 554 is turned off, or when an AC power line failure occurs.

The subsection detailing timer circuit 514 is primarily comprised of an oscillator, two binary counters, and associated logic gates. Integrated circuit counter 570, preferably a 14-stage ripple-carry binary counter available from Motorola (type CD4060B), can be configured to utilize its input stages as a dual-invertor R-C oscillator. A switch 572 is used for testing purposes, to disable the oscillator. When switch 572 is closed, the frequency of the oscillator is primarily determined by the values of resistor 574 (150 K) and Capacitor 578 (1 uF). In the preferred embodiment, the oscillator operates at approximately 3.25 Hertz. A resistor 576 (120 K) completes the oscillator by coupling the R-C timing signal back to the input of the first invertor. A diode 580 is used to disable the oscillator circuit upon the expiration of the thirty-day time period, the details of which will be described below.

A NAND gate 582 is coupled to the $Q_{12}$ output (pin 1) and the $Q_{13}$ output (pin 2) of counter IC 570, respectively. The $Q_{12}$ output (divide-by 4096) provides a signal having a period of 21 minutes. The $Q_{13}$ output (divide-by 8192) provides a signal having a period of 42 minutes. Once these two outputs are combined together at NAND gate 582, the output at 584 generates at first switch control signal, labeled waveform B. The waveform diagram of FIG. 24 shows this NAND gate output as waveform B. Note that this first control signal goes high for approximately 31.5 minutes and low for approximately 10.5 minutes, i.e., exhibiting a 75% duty cycle.

This first control signal is applied to resistor divider network 586 (39 K) and 588 (4.7 K), and applied as the gate current to drive the silicon controlled rectifier used as switching device 510. Hence, as shown by the heating element waveform E of FIG. 24, the switch 510 is turned on and off with a duty cycle of 75%. Waveform E illustrates that the 60 Hertz half-wave voltage at the heating element is not switched to ground during the 31.5 minutes in which the SCR is conducting, since resistor 508 drops some of the voltage, depending upon its resistance value with respect to the resistance of the heating element. In the example shown, the total resistance of both elements in heating element 506 is approximately 1500 ohms. Since resistor 508 is 150 ohms, then approximately 1/11th of the half-wave rectified AC voltage applied to the diffuser is dissipated across resistor 508.

Integrated circuit 560 is also a 14-stage ripple-carry binary counter (Motorola type CD4020B), which is similar to IC 570 only without the oscillator. The output signal of NAND gate 582 is used as a clock input signal to counter IC 560. Accordingly, the $Q_9$ (divide-by 512) output (at pin 12) of IC 560 provides a 15 day/cycle timing signal. Similarly, the $Q_{10}$ (divide-by 1024) output (at pin 14) provides a 30 day/cycle timing signal.

The $Q_9$ output signal is routed through diode 590 and resistor 592 (56 K) to one input of NAND gate 594, while the other input of NAND gate 594 is connected to the clock signal waveform B. The output of NAND gate 594 is applied to both inputs of NAND gate 596, which is connected as an invertor. The output of NAND gate 596 is applied to diode 598, which provides a high control signal to the resistor divider network 606 (22 K), 608 (4.7 K) attached to the gate of the SCR which serves as switch 512. Similarly, the $Q_{10}$ output of counter IC 560 is routed through diode 600, resistor 602

(12 K), and diode 604 to supply a high control signal at the junction of diodes 604 and 598. This junction is labelled waveform C in FIG. 24. Diodes 590, 600 and resistors 592, 602 ensure that switch 512 is turned off and that NAND gate 594 is not powered-up via counter IC 560 when V+ is removed.

As shown in FIG. 24, the control signal for switch 512, represented by waveform C, is low for the first cycle of 7 days. The SCR representing switch 512 is turned off during this time, while switch 510 controls the voltage applied to heating element 506 through resistor 508. Hence, the heating element is on for 31.5 minutes at reduced power, and then shuts off for 10.5 minutes during the first 7 day cycle.

During the second 7 day cycle, waveforms B & C are effectively in phase, such that switch 512 turns on during the high signal portions of the 31.5/10.5 minute duty cycle. As shown in waveform E, all the voltage is now being applied to heating element 506, such that resistor 508 and switch 510 are effectively out of the circuit. Hence, the heating element is on for 31.5 minutes at full power, and then shuts off for 10.5 minutes during the second 7 day cycle.

During the third cycle of 15 days, the control signal of waveform C is constantly high, such that switch 512 is constantly on. Again, all the power is being dissipated by heating element 506. However, the duty cycle has been increased to 100%. Hence, the heating element is constantly on at full power from the 15th day to the 30th day.

After 30 days, which is the approximate life cycle of a fragrance block, the $Q_{11}$ (divide-by 2048) output (pin 15) of counter IC 560 goes high, such that the V+ voltage through resistor 610 (56 K) is no longer being pulled low by diode 612. Accordingly, the output of NAND gate 614, which is configured as an invertor, goes low, as shown in waveform D of FIG. 24. The NAND output voltage going low causes the oscillation to stop (via diode 580), and turns on red LED 616 through resistor 618 (4.7 k). The activation of the red LED signals to the user that the 30 day time period has expired. Moreover, once the oscillation stops, the heating element is turned off. The diffuser circuit will maintain this state until the reset button is pressed.

Normally, the reset pin (pin 12) of counter IC 570 and the reset pin (pin 11) of counter IC 560 are both held low by resistors 622 (22 k) and 628 (10 M). However, when the reset switch 560 is momentarily pressed, the reset voltage goes high, as illustrated in waveform A of FIG. 24. This reset signal immediately resets counter IC 570. This high reset voltage also slowly charges a capacitor 624 (0.1 uF) through resistor 628 (10 M), such that this delay circuit requires the reset button to be held closed for at least two seconds to reset counter IC 560. Diode 626 is used to quickly discharge capacitor 624. Thus, if the reset button is held closed for less than two seconds, all the outputs of counter IC 570 are reset to zero, which forces the output of NAND gate 582 high, such that switch 510 is constantly on. Recall that since counter IC 560 has not also been reset, the voltage of waveform D is still low, and the oscillator is still disabled. Hence, heating element 506 will be constantly on, at a reduced power level.

However, pressing on reset switch 620 for two seconds or more will reset both counters. If this occurs, all the outputs of counter IC 560 are also reset to zero, which forces the output of NAND gate 614 high, such that the red LED 616 is extinguished and the oscillator is again enabled. The two second delay in the reset operation prevents resetting of the timing period due to accidental bumping of the reset switch. Moreover, it provides the user with the option to keep using the same fragrance cartridge beyond its 30 day life cycle.

Waveform I of FIG. 24 represents the half-wave rectified current through heating element 506. This waveform provides a good illustration of the operation of the heater circuit 540. During the first 7 days after a reset occurs, switch 510 is operated at a 75% duty cycle to provide a current path through heating element 506 and resistor 508. In the preferred embodiment, the AC supply is 120 VAC RMS, the heating element is approximately 1500 ohms, and resistor 508 is 150 ohms. Thus, the half-wave rectified AC power is dissipated by the 1650 ohms total resistance such that 72 milliamps flows through the circuit. This translates into 4.0 watts of dissipation for heating element 506, and 0.4 watts for resistor 508, or a total dissipation for the fragrance diffuser of approximately 4.4 watts. As shown in waveform I, the current varies between a zero level and a level corresponding to 72 milliamps at 60 Hz. However, recall that switch 510 is operating at a 75% duty cycle. Therefore, the average power dissipated by heating element 506 during the first cycle is approximately 3.0 watts.

During the second cycle of 7 days, switch 512 operates to switch the full supply voltage across the heating element. Accordingly, the current through heating element 506 is 80 milliamps, which translates to 4.8 watts. Again, since the switch is operating at a 75% duty cycle, approximately 3.6 watts are being dissipated by the heating element.

Finally, during the third cycle of 15 days, switch 512 is constantly on, such that 80 milliamps is constantly flowing through heating element 506. This translates into a constant dissipation of approximately 4.8 watts.

In review, it can now be seen that the present invention provides a method and apparatus for adjusting the fragrance level over the life of a replaceable aroma-bearing cartridge. Since the fragrance level of a new cartridge is strongest within the first few days of operation, low power is applied to the heating element such that a lower temperature is used to enhance the diffusion of the aroma-bearing media into the air. The power to the heating element, and consequently the temperature of the heating element, is increased with time. As previously discussed, the voltage to the heating element can be increased in two, three, or more individual discrete steps. Moreover, the duty cycle of operation or the conduction angle of an SCR can be linearly increased to provide continuously variable control of the power to the heating element. Furthermore, any of the various circuit configurations illustrated above, or modifications thereof, can be used to perform the function of increasing the power over time.

The above-described embodiments of the invention are merely examples of ways in which the invention may be carried out. Other ways may also be possible. For example, various keying schemes may be used to achieve the same goal of keying fragrance blocks to diffuser chambers. Hence, the claims should be construed to include all equivalent structures which are within the scope and spirit of the invention.

What is claimed is:
1. An aroma dispenser comprising:
 means for emitting a fragrance when heated;

heater means for providing electric heating for said fragrance emitting means in response to electric power;

timer means for determining when a predetermined period of time has lapsed and for providing a timing signal in response thereto; and means for automatically controlling the average amount of electric power applied to said heater means by varying the average power level between a first average power level and a second average power level in response to said timing signal, at least one of said first and second average power levels being a partial average power level which is less than maximum available power and is greater than no power 2. The aroma dispenser according to claim 1, wherein said controlling means increases the average electric power to said heater means when said predetermined period of time has lapsed.

3. The aroma dispenser according to claim 2, wherein said fragrance emitting means has a limited useful life, and wherein said predetermined period of time corresponds to less than half of said useful life.

4. The aroma dispenser according to claim 3, wherein said timer means includes a light emitting diode for indicating to the user when said useful life has expired.

5. The aroma dispenser according to claim 1, wherein said fragrance emitting means includes an expendable solid cartridge containing a diffusible aroma-bearing media.

6. The aroma dispenser according to claim 1, wherein said heater means includes a resistive heating element.

7. The aroma dispenser according to claim 1, wherein said heater means includes a plurality of heating elements each individually controlled by said controlling means.

8. The aroma dispenser according to claim 1, wherein said controlling means includes a resistor connected in series with at least a portion of said heater means.

9. The aroma dispenser according to claim 1, wherein said controlling means includes a diode connected in series with at least a portion of said heater means.

10. The aroma dispenser according to claim 1, wherein said controlling means includes a silicon controlled rectifier connected in series with at least a portion of said heater means.

11. The aroma dispenser according to claim 1, wherein said controlling means includes a triac connected in series with at least a portion of said heater means.

12. The aroma dispenser according to claim 1, wherein said timer means is an electronic timer circuit capable of determining periods of time greater than 24 hours.

13. The aroma dispenser according to claim 12, wherein said predetermined period of time is greater than three days.

14. The aroma dispenser according to claim 1, wherein said timer means provides a first timing signal after approximately seven and one-half days, and produces a second timing signal after approximately fifteen days.

15. The aroma dispenser according to claim 1, wherein said controlling means includes a phase-controllable electronic switching device and an electronic circuit for controlling the conduction angle of said electronic switching device, such that when said conduction angle is increased the average electric power applied to said heater means is increased.

16. The aroma dispenser according to claim 1, wherein said controlling means includes an electronic switching device and an electronic circuit for controlling the duty cycle of said electronic switching device, such that when said duty cycle is increased the average electric power applied to said heater means is increased.

17. The aroma dispenser according to claim 1, wherein said controlling means includes an electronic switching device and a resistor connected to said heater means such that the power-reducing effect of said resistor is effectively eliminated when said switching device is activated in response to said timing signal, thereby increasing the power to said heater means.

18. The aroma dispenser according to claim 1, wherein said timer means includes:

oscillator means for producing a plurality of intermediate signals;

means for counting a predetermined number of said intermediate signals, thereby producing a timing signal when said predetermined number has been reached; and disabling means, responsive to said timing signal, for inhibiting operation of said oscillator means until a reset signal is received.

19. The aroma dispenser according to claim 1, further comprising housing means for containing said fragrance emitting means, and wherein the removal of said fragrance emitting means from said housing means does not affect said timer means.

20. The aroma dispenser according to claim 18, wherein said timer means includes means for preventing said counting means from being reset when power is removed from said aroma dispenser.

21. The aroma dispenser according to claim 1, wherein said timer means operates independently of temperature.

22. The aroma dispenser according to claim 1, wherein said timer means includes means for determining when a plurality of predetermined periods of time have lapsed, and for providing a plurality of timing signals in response thereto.

23. The aroma dispenser according to claim 22, wherein said controlling means includes means for varying the average power level between a first average power level, a second average power level, and a third average power level in response to said plurality of timing signals.

24. The aroma dispenser according to claim 23, wherein said first and second average power levels are both partial average power levels being greater than half power.

25. The aroma dispenser according to claim 1, wherein said first average power level is greater than approximately half power but less than approximately full power, and wherein said second average power level is approximately full power.

26. The aroma dispenser according to claim 1, wherein said controlling means increases the average amount of electric power applied to said heater means in a series of sequential steps between a first, second, and third average power level, at least said second average power level being a partial average power level less than full power but greater than half power.

27. A fragrance dispenser adapted for use with an expendable cartridge means for emitting a fragrance into the air when heated, said cartridge means having a predefined expected useful life, said fragrance diffuser comprising:

housing means for receiving and containing said cartridge means;

heater means for providing electric heating of said cartridge means in response to electric power;

timer means for indicating when a predetermined period of time of operation of said heater means has lapsed, said timer means operating independently of temperature;

means for partially reducing said electric power applied to said heater means;

means for automatically controlling said heater means and said power reducing means in response to said timer means such that the amount of heat provided to said cartridge means is increased after said predetermined period of time of operation has lapsed.

28. The fragrance dispenser according to claim 27, wherein said power reducing means is a resistor.

29. The fragrance dispenser according to claim 27, wherein said power reducing means is a diode.

30. The fragrance dispenser according to claim 27, wherein said controlling means is a silicon controlled rectifier.

31. The fragrance dispenser according to claim 27, wherein said controlling means is a triac.

32. The fragrance dispenser according to claim 27, wherein said controlling means switches power directly to said heater means in response to said timer means without connecting said power reducing means.

33. The fragrance dispenser according to claim 22, wherein said controlling means includes two electronic switching devices, one connected directly in series with said heater means, the other connected in series with said heater means through said power reducing means.

34. The fragrance dispenser according to claim 27, wherein said controlling means includes means for controlling the duty cycle of the electronic power applied to said heater means.

35. The fragrance dispenser according to claim 27, wherein said timer means provides a plurality of sequential timing signals, and wherein said controlling means increases the amount of electric power applied to said heater means in sequential steps.

36. The fragrance dispenser according to claim 35, wherein said controlling means increases the average amount of electric power applied to said heater means in a series of sequential steps between a first, second, and third average power level, at least one of said power levels being a partial average power level less than full power but greater than half power.

37. In a fragrance diffuser having an electric heating element and a replaceable fragrance-bearing cartridge, said cartridge having a limited useful life, the method of adjusting the fragrance level over the life of said cartridge comprising the steps of:

(a) heating the cartridge to a first temperature level;

(b) providing a first timing signal upon the expiration of a first period of time; and (c) heating said cartridge to a second temperature level which is higher than said first temperature level in response to said first timing signal.

38. The method according to claim 37, further comprising the steps of:

(d) providing a second timing signal upon the expiration of a second period of time; and (e) heating said cartridge to a third temperature level which is higher than said second temperature level in response to said second timing signal.

39. The method according to claim 37, wherein said heating element is connected in a series circuit with a power-reducing element, the method further comprising the step of bypassing the power-reducing element from the series circuit in response to said first timing signal.

40. The method according to claim 37, further comprising the steps of:

providing a first timing signal after less than ten days; and increasing the power applied to said heating element after the occurrence of said first timing signal.

41. The method according to claim 40, further comprising the steps of:

providing a second timing signal after less than twenty days; and increasing the power applied to said heating element after the occurrence of said second timing signal.

42. The method according to claim 41, further comprising the steps of:

providing a third timing signal after greater than thirty days; and disconnecting electric power from said heating element in response to said third timing signal.

43. The method according to claim 37, further comprising the step of:

providing a reset signal to initialize said first period of time only after a delay of at least one second has elapsed after the activation of a reset switch.

* * * * *